(12) United States Patent
Hutchinson et al.

(10) Patent No.: US 11,235,036 B2
(45) Date of Patent: Feb. 1, 2022

(54) LYSOSOMAL ACID LIPASE DEFICIENCY COMPOSITIONS AND METHODS

(71) Applicant: ALEXION PHARMACEUTICALS, INC., Boston, MA (US)

(72) Inventors: Andrew Hutchinson, Stamford, CT (US); John V. W. Reynders, Newton, MA (US); Guillermo del Angel, Lexington, MA (US); Nina Jain, North Andover, MA (US); Christen D. Forbes, North Haven, CT (US); Xiao-Qin Ren, North Attleboro, MA (US); Barbara Burton, Chicago, IL (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 196 days.

(21) Appl. No.: 16/308,558

(22) PCT Filed: Jun. 16, 2017

(86) PCT No.: PCT/US2017/037928
§ 371 (c)(1),
(2) Date: Dec. 10, 2018

(87) PCT Pub. No.: WO2017/218926
PCT Pub. Date: Dec. 21, 2017

(65) Prior Publication Data
US 2019/0151420 A1 May 23, 2019

Related U.S. Application Data

(60) Provisional application No. 62/351,631, filed on Jun. 17, 2016, provisional application No. 62/358,951, filed on Jul. 6, 2016, provisional application No. 62/457,356, filed on Feb. 10, 2017.

(51) Int. Cl.
| | | |
|---|---|---|
| *C12Q 1/6883* | (2018.01) | |
| *A61K 38/46* | (2006.01) | |
| *C12N 9/20* | (2006.01) | |
| *A61P 1/02* | (2006.01) | |
| *A61P 1/16* | (2006.01) | |
| *C12Q 1/6853* | (2018.01) | |
| *C12Q 1/6858* | (2018.01) | |
| *C40B 40/08* | (2006.01) | |

(52) U.S. Cl.
CPC ............ *A61K 38/465* (2013.01); *A61P 1/02* (2018.01); *A61P 1/16* (2018.01); *C12N 9/20* (2013.01); *C12Q 1/6853* (2013.01); *C12Q 1/6858* (2013.01); *C12Q 1/6883* (2013.01); *C12Y 301/01013* (2013.01); *C12Q 2600/156* (2013.01); *C12Y 301/01003* (2013.01); *C40B 40/08* (2013.01)

(58) Field of Classification Search
None
See application file for complete search history.

(56) References Cited

U.S. PATENT DOCUMENTS

| | | |
|---|---|---|
| 8,663,631 B2 | 3/2014 | Quinn |
| 2012/0064055 A1 | 3/2012 | Quinn |
| 2013/0020943 A1 | 8/2013 | Quinn et al. |
| 2014/0155475 A1 | 6/2014 | Bancel et al. |
| 2014/0348752 A1 | 11/2014 | Quinn |
| 2016/0005163 A1 | 2/2016 | Quinn |
| 2019/0151420 A1 | 5/2019 | Hutchinson et al. |

FOREIGN PATENT DOCUMENTS

| | | |
|---|---|---|
| WO | WO 2011/133960 A2 | 10/2011 |
| WO | WO 2012/050695 A1 | 4/2012 |
| WO | WO 2012/112677 A2 | 8/2012 |
| WO | WO 2012/112681 A1 | 8/2012 |
| WO | WO 2017/218926 A1 | 12/2017 |

OTHER PUBLICATIONS

Reiner et al. Lysosomal acid lipase deficiency e An under-recognized cause of dyslipidaemia and liver dysfunction. Atherosclerosis; 2014; 235; 21-30. (Year: 2014).*
Reiner 2014 supplemental data, p. 1-17. Reiner et al. Lysosomal acid lipase deficiency e An under-recognized cause of dyslipidaemia and liver dysfunction. Atherosclerosis; 2014; 235; 21-30. (Year: 2014).*
Hooper et al. A novel missense LIPA gene mutation, N98S, in a patient with cholesteryl ester storage disease. Clinica Chimica Acta ; 2008; 398: 152-154. (Year: 2008).*
Kuranobu et al. Cholesterol ester storage disease with a novel LIPA mutation (L264P) that presented massive hepatomegaly: A case report. Hepatology Research; Mar. 2016; 46: 477-482, Epub on Sep. 17, 2015. (Year: 2015).*
Scott et al. Frequency of the Cholesteryl Ester Storage Disease Common LIPA E8SJM Mutation (c.894G>A) in Various Racial and Ethnic Groups. Hepatology; 2013;58(3): 958-965. (Year: 2013).*
Ameis et al., "A 5' splice-region mutation and a dinucleotide deletion in the lysosomal acid lipase gene in two patients with cholesteryl ester storage disease," Feb. 1995, *The Journal of Lipid Research*, 36:241-250.
Anderson et al., "Cloning and expression of cDNA encoding human lysosomal acid lipase/cholesteryl ester hydrolase. Similarities to gastric and lingual lipases," Nov. 25, 1991, *The Journal of Biological Chemistry*, 266:22479-22484.
Anderson et al., "Mutations at the lysosomal acid cholesteryl ester hydrolase gene locus in Wolman disease," Mar. 1994, *Proceedings of the National Academy of Sciences of the United States of America*, 91:2718-2722.

(Continued)

Primary Examiner — Juliet C Switzer
Assistant Examiner — Wahwah T Johnson
(74) *Attorney, Agent, or Firm* — Clark & Elbing LLP

(57) ABSTRACT

Compositions and methods relating to potentially pathogenic mutations in the nucleotide sequence of a human LIPA gene. Some LIPA gene products have been discovered to be associated with reduced lysosomal acid lipase (LAL) activity.

21 Claims, 8 Drawing Sheets
Specification includes a Sequence Listing.

(56) References Cited

OTHER PUBLICATIONS

Anderson et al., "Lysosomal acid lipase mutations that determine phenotype in Wolman and cholesterol ester storage disease," Nov. 1999, *Molecular Genetics and Metabolism*, 68:333-345.
Anonymous, "ExAC Browser Gene:LIPA," Jan. 1, 2016, Retrieved from the Internet: URL: http://exac.broadinstitute.org/gene/ENSG00000107798 [retrieved on Sep. 21, 2017].
Anonymous, "Lyososomal Acid Lipase Deficiency," Retrieved from the Internet URL: http://omim.org/entry/278000 [retrieved on Jun. 28, 2019].
Aslanidis et al., "Genetic and biochemical evidence that CESD and Wolman disease are distinguished by residual lysosomal acid lipase activity," Apr. 1, 1996, *Genomics*, 33:85-93.
Azam et al., "Investigation of novel chemical inhibitors of human lysosomal acid lipase: virtual screening and molecular docking studies," 2014, *Combinatorial Chemistry & High Throughput Screening*, 17(5):473-482.
Balwani et al., "Clinical effect and safety profile of recombinant human lysosomal acid lipase in patients with cholesteryl ester storage disease," Sep. 2013, *Hepatology*, 58(3):950-7.
Bernstein et al., "Cholesteryl ester storage disease: review of the findings in 135 reported patients with an underdiagnosed disease," Jun. 2013, *Journal of Hepatology*, 5 8(6): 1230-1243.
Burton et al., "Lysosomal acid lipase in cultivated fibroblasts: Characterization of enzyme activity in normal and enzymatically deficient cell lines," Feb. 14, 1980 *Clinica Chimica Acta*, 101:25-32.
Burton et al., "A Phase 3 Trial of Sebelipase Alfa in Lysosomal Acid Lipase Deficiency," Sep. 10, 2015, *The New England Journal of Medicine*, 373:1010-1020.
Burton et al., "Clinical Features of Lysosomal Acid Lipase Deficiency," Dec. 2015, *Journal of Pediatric Gastroenterology and Nutrition*, 61(6):619-625.
CCDS Report for Consensus CDS, "Report for CCDS7401.1 (current version)," obtained online Jun. 28, 2019, <URL:https://www.ncbi.nlm.nih.gov/CCDS/CcdsBrowse.cgi?REQUEST=CCDS&DATA=CCDS7401>.
Chial et al., "Rare Genetic Disorders: Learning About Genetic Disease Through Gene Mapping, SNPs, and Microarray Data," 2008, *Nature Education*, 1(1): 192.
Clinical Trial: A Multicenter Study of SBC-102 (Sebelipase Alfa) in Patients With Lysosomal Acid Lipase Deficiency/ ARISE (Acid Lipase Replacement Investigating Safety and Efficacy). Study Details Datasheet [online]. First Posted Dec. 28, 2012 [retrieved on Jun. 28, 2019], Retrieved from the Internet: <URL:https://clinicaltrials.gov/ct2/show/NCT01757184>. 7 pages.
Clinical Trial: Safety and Efficacy Study of Sebelipase Alfa in Participants With Lysosomal Acid Lipase Deficiency. Study Details Datasheet [online]. First Posted Apr. 14, 2014 [retrieved on Jun. 28, 2019], Retrieved from the Internet: <URL: https://clinicaltrials.gov/ct2/show/NCT02112994>. 6 pages.
del Angel et al., "Large-scale functional LIPA variant characterization to improve birth prevalence estimates of lysosomal acid lipase deficiency," Jan. 31, 2019, *Human Mutation*, 1-14.
den Dunnen et al., "Mutation Nomenclature Extensions and Suggestions to Describe Complex Mutations: a discussion," Nov. 2000, *Human Mutation*, 15:7-12.
Doolittle et al., "Lipase and Phospholipase Protocols" in *Meth. Mol. Biol., Human Press*, 1999, 109:98-102.
Drebber et al., "Severe chronic diarrhea and weight loss in cholesteryl ester storage disease: a case report," Apr. 21, 2005, *World Journal of Gastroenterology*, 11:2364-2366.
Du et al., "Molecular and enzymatic analyses of lysosomal acid lipase in cholesteryl ester storage disease," Jun. 1998, *Molecular Genetics and Metabolism*, 64:126-134.
Elleder et al., "Subclinical course of cholesteryl ester storage disease in an adult with hypercholesterolemia, accelerated atherosclerosis, and liver cancer," Mar. 2000, *Journal of Hepatology*, 32:528-534.

ExAC Browser (Beta)—Exome Aggregation Consortium (/about), obtained online Jun. 28, 2019, <URL:exac.broadinstitute.org>.
Fasano et al., "Lysosomal lipase deficiency: molecular characterization of eleven patients with Wolman or cholesteryl ester storage disease," Mar. 2012, *Molecular Genetics and Metabolism*, 105:450-456.
Fujiyama et al., "A new mutation (LIPA Tyr22X) of lysosomal acid lipase gene in a Japanese patient with Wolman disease," 1996, *Human Mutation*, 8:377-380.
Gasche et al., "A novel variant of lysosomal acid lipase in cholesteryl ester storage disease associated with mild phenotype and improvement on lovastatin," Oct. 27, 1997, *Journal of Hepatology*, 27:744-750.
Grabowski et al., "Lysosomal Acid Lipase Deficiencies: The Wolman Disease/Cholesteryl Ester Storage Disease Spectrum," in *The Online Metabolic & Molecular Bases of Inherited Disease*, Beaudet et al. (Ed.) McGraw-Hill: Colombus, OH; 2012. part 16, chapter 142, pp. 1-9.
Hamilton et al., "A new method for the measurement of lysosomal acid lipase in dried blood spots using the inhibitor Lalistat 2P," Aug. 16, 2012, *Clinica Chimica Acta*, 413(15-16)1207-1210.
Haznedar et al., "A rare cause of hepatomegaly in the childhood: Lysosomal acid lipase deficiency," Jun. 26, 2018, *Turk J Gastroenterol*, 29:518-9.
Hoffman et al., "Lysosomal Acid Lipase Deficiency," in *GeneReviews®* [Internet], Pagon et al. (Ed.) University of Washington: Seattle, WA; 2015 1993-2016.
Hooper et al., "A novel missense LIPA gene mutation, N98S, in a patient with cholesteryl ester storage disease.," Dec. 2008, *Clinica Chimica*, 398:152-154.
Huang et al., "Wolman disease with novel mutation of LIPA gene in a Chinese infant," Aug. 2012, *Zhonghua Er.Ke.Za Zhi*, 50:601-605.
Hutchinson et al., "Functional characterization of novel LIPA variants found within the ExAC database," Abstract, The Metabolic Role of the Lysosome and Nutrient Sensing Conference, (Zing Conferences CIC) Cambridge, United Kingdom, Jul. 9-12, 2016.
Hutchinson et al., "Functional characterization of novel LIPA variants found within the ExAC database," Poster, The Metabolic Role of the Lysosome and Nutrient Sensing Conference (Zing Conferences CIC) Cambridge, United Kingdom, Jul. 9-12, 2016.
International Patent Application No. PCT/US2017/037928, filed Jun. 16, 2017; International Search Report / Written Opinion dated Nov. 29, 2017; 23 pages.
International Patent Application No. PCT/US2017/037928, filed Jun. 16, 2017 Office Action dated Dec. 27, 2018.
Kanuma-International non-proprietary name: sebelipase alfa, "Assessment Report," European Medicines Agency—Science Medicines Health, Jun. 25, 2015, retrieved online Jun. 28, 2019, 87 pages.
Klima et al., "A splice junction mutation causes deletion of a 72-base exon from the mRNA for lysosomal acid lipase in a patient with cholesteryl ester storage disease," Dec. 1993, *The Journal of Clinical Investigation*, 92 (6):2713-2718.
Kuranobu et al., "Cholesterol ester storage disease with a novel LIPA mutation (L264P) that presented massive hepatomegaly: A case report," Mar. 2016, *Hepatology research: the official journal of the Japan Society of Hepatology*, 46(5):477-82.
Lee et al., "Intragenic deletion as a novel type of mutation in Wolman disease," Dec. 2011, *Molecular Genetics and Metabolism*, 104:703-705.
Lohse et al., "Human lysosomal acid lipase/cholesteryl ester hydrolase and human gastric lipase: identification of the catalytically active serine, aspartic acid, and histidine residues," May 1997, *The Journal of Lipid Research*, 38:892-903.
Lohse et al., "Molecular defects underlying Wolman disease appear to be more heterogeneous than those resulting in cholesteryl ester storage disease," Feb. 1999, *The Journal of Lipid Research*, 40:221-228.
Lohse et al., "Compound heterozygosity for a Wolman mutation is frequent among patients with cholesteryl ester storage disease," Jan. 2000, *The Journal of Lipid Research*, 41:23-31.
Maslen et al., "Occurrence of a mutation associated with Wolman disease in a family with cholesteryl ester storage disease," 1995, *Journal of Inherited Metabolic Disease*, 18:620-623.

(56) References Cited

OTHER PUBLICATIONS

Mayatepek et al., "Fatal genetic defect causing Wolman disease," 1999, *Journal of Inherited Metabolic Disease*, 22:93-94.
Muntoni et al., "Homozygosity for a splice junction mutation in exon 8 of the gene encoding lysosomal acid lipase in a Spanish kindred with cholesterol ester storage disease (CESD)," May 1995, *Human Genetics*, 95:491-494.
National Center for Biotechnology Information, National Library of Medicine, National Institutes of Health, GenBank Locus NM_000235. 4, Accession No. NM_000235, "*Homo sapiens* lipase A, lysosomal acid type (LIPA), transcriptvariant 2, mRNA," [online], Bethesda, MD [retrieved on Jun. 28, 2019], Retrieved from the Internet:<https://www.ncbi.nlm.nih.gov/nuccore/NM_000235>, 4 pages.
National Center for Biotechnology Information, National Library of Medicine, National Institutes of Health, GenBank Locus NP_001121077, Accession No. NP_001121077, "lysosomal acid lipase/cholesteryl ester hydrolase isoform 1precursor [*Homo sapiens*].," [online], Bethesda, MD [retrieved on Jun. 28, 2019], Retrieved from the Internet: <https://www.ncbi.nlm.nih.gov/protein/NP_001121077. 1>, 3 pages.
National Center for Biotechnology Information, National Library of Medicine, National Institutes of Health, GenBank Locus NM_000235, Accession No. NM_000235.3, "*Homo sapiens* lipase A, lysosomal acid type (LIPA), transcript variant 2, mRNA," [online], Bethesda, MD [retrieved on Jun. 28, 2019], Retrieved from the Internet: < https://www.ncbi.nlm.nih.gov/nuccore/NM_000235.3>, 5 pages.
National Center for Biotechnology Information, National Library of Medicine, National Institutes of Health, GenBank Locus NM 001127605.2, "NM_001127605.2(LIPA):c.260G>T (p.Gly87Val) and Lysosomal acid lipase deficiency," [online], Bethesda, MD [retrieved on Jun. 28, 2019], Retrieved from the Internet: < https://www.ncbi.nlm.nih.gov/clinvar/41154878/>, 2 pages.
Ogino et al., "Standard Mutation Nomenclature in Molecular Diagnostics," Feb. 2007, *Journal of Molecular Diagnostics*, 9:1-6.
Pabinger et al., "A survey of tools for variant analysis of next-generation genome sequencing data," Mar. 15, 2014, *Briefings in Bioinformatics*, 15(2):256-278.
Pagani et al., "A histidine to tyrosine replacement in lysosomal acid lipase causes cholesteryl ester storage disease," Sep. 1994, *Human Molecular Genetics*, 3:1605-1609.
Pagani et al., "Expression of lysosomal acid lipase mutants detected in three patients with cholesteryl ester storage disease," Oct. 1996, *Human Molecular Genetics*, 5:1611-1617.
Pagani et al. "New lysosomal acid lipase gene mutants explain the phenotype of Wolman disease and cholesteryl ester storage disease." *J.LipidRes.* 1998, 39:1382-1388.
Pisciotta et al., "Cholesteryl Ester Storage Disease (CESD) due to novel mutations in the LIPA gene," Jun. 2009, *Molecular Genetics and Metabolism*, 97:143-148.
Redonnet-Vernhet et al., "Cholesteryl ester storage disease: relationship between molecular defects and in situ activity of lysosomal acid lipase.," Oct. 1997, *Biochemical and Molecular Medicine*, 62:42-49.

Reiner et al., "Lysosomal acid lipase deficiency—an under-recognized cause of dyslipidaemia and liver dysfunction," Jul. 2014, *Atherosclerosis*, 235(1):21-30.
Reynders et al., "Novel LIPA Mutations Resulting in Lysosomal Acid Lipase Deficiency," Jan. 1, 2017, *Molecular Genetics and Metabolism*, vol. 120, No. 1-2, S114-S115.
Ries et al., "A new mutation in the gene for lysosomal acid lipase leads to Wolman disease in an African kindred," Aug. 1996, *Journal of Lipid Research*, 37:1761-1765.
Ries et al., "Different missense mutations in histidine-108 of lysosomal acid lipase cause cholesteryl ester storage disease in unrelated compound heterozygous and hemizygous individuals," 1998, *Human Mutation*, 12:44-51.
Roussel et al., "Crystal Structure of Human Gastric Lipase and Model of Lysosomal Acid Lipase, Two Lipolytic Enzymes of Medical Interest," Jun. 11, 1999 *The Journal of Biological Chemistry*, 274(24):16995-17002.
Roussel et al., "Crystal structure of the open form of dog gastric lipase in complex with a phosphonate inhibitor," Jan. 18, 2002, *The Journal of Biological Chemistry*, 277(3):2266-2274.
Saito et al., "Structural bases of Wolman disease and cholesteryl ester storage disease," Feb. 2012, *Molecular Genetics and Metabolism*, 105:244-248.
Sando et al., "Human lysosomal acid lipase/cholesteryl ester hydrolase. Purification and properties of the form secreted by fibroblasts in microcarrier culture," Dec. 5, 1985, *The Journal of Biological Chemistry*, 260(28):15186-93.
Santillan-Hernandez et al., "Novel LIPA mutations in Mexican siblings with lysosomal acid lipase deficiency," Jan. 21, 2015, *World Journal of Gastroenterology*, 21(3): 1001-8.
Scott et al., "Frequency of the cholesteryl ester storage disease common LIPA E8SJM mutation (c.894G>A) in various racial and ethnic groups," Sep. 2013, *Hepatology*, 58(3):958-65.
Seedorf et al., "A novel variant of lysosomal acid lipase (Leu336—>Pro) associated with acid lipase deficiency and cholesterol ester storage disease.," Jun. 1995, *Arteriosclerosis, Thrombosis, and Vascular Biology*, 15:773-778.
Selvan et al., "Molecular dynamics simulations of human and dog gastric lipases: Insights into domain movements," Nov. 19, 2010, *FEBS letters*, 584(22):4599-605.
Sheriff et al., "Characterization of lysosomal acid lipase by site-directed mutagenesis and heterologous expression," Nov. 17, 1995, *The Journal of Biological Chemistry*, 270:27766-27772.
Valayannopoulos et al., "Sebelipase alfa over 52 weeks reduces serum transaminases, liver volume and improves serum lipids in patients with lysosomal acid lipase deficiency," Nov. 2014, *Journal of Hepatology*, 61(5):1135-42.
Zschenker et al., "Characterization of lysosomal acid lipase mutations in the signal peptide and mature polypeptide region causing Wolman disease," July 200, *Journal of Lipid Research*, 42:1033-1040.

* cited by examiner

```
   1 ATGAAAATGCGGTTC TTGGGGTTGGTGGTC TGTTTGGTTCTCTGG ACCCTGCATTCTGAG
   1  M  K  M  R  F   L  G  L  V  V    C  L  V  L  W    T  H  S  E
  61 GGGTCTGGAGGGAAA CTGACAGCTGTGGAT CCTGAAACAAACATG AATGTGAGTGAAATT
  21  G  S  G  G  K   L  T  A  V  D    P  E  T  N  M    N  V  S  E  I
 121 ATCTCTTACTGGGGA TTCCCTAGTGAGGAA TACCTAGTTGAGACA GAAGATGGATATATT
  41  I  S  Y  W  G   F  P  S  E  E    Y  L  V  E  T    E  D  G  Y  I
 181 CTGTGCCTTAACCGA ATTCCTCATGGGAGG AAGAACCATTCTGAC AAAGGTCCCAAACCA
  61  L  C  L  N  R   I  P  H  G  R    K  N  H  S  D    K  G  P  K  P
 241 GTTGTCTTCCTGCAA CATGGCTTGCTGGCA GATTCTAGTAACTGG GTCACAAACCTTGCC
  81  V  V  F  L  Q   H  G  L  L  A    D  S  S  N  W    V  T  N  L  A
 301 AACAGCAGCCTGGGC TTCATTCTTGCTGAT GCTGGTTTTGACGTG TGGATGGGCAACAGC
 101  N  S  S  L  G   F  I  L  A  D    A  G  F  D  V    W  M  G  N  S
 361 AGAGGAAATACCTGG TCTCGGAAACATAAG ACACTCAGTTTCT CAGGATGAATTCTGG
 121  R  G  N  T  W   S  R  K  H  K    T  L  S  V  S    Q  D  E  F  W
 421 GCTTTCAGTTATGAT GAGATGGCAAAATAT GACCTACCAGCTTCC ATTAACTTCATTCTG
 141  A  F  S  Y  D   E  M  A  K  Y    D  L  P  A  S    I  N  F  I  L
 481 AATAAAACTGGCCAA GAACAAGTGTATTAT GTGGGTCATTCTCAA GGCACCACTATAGGT
 161  N  K  T  G  Q   E  Q  V  Y  Y    V  G  H  S  Q    G  T  T  I  G
 541 TTTATAGCATTTTCA CAGATCCCTGAGCTG GCTAAAAGGATTAAA ATGTTTTTTGCCCTG
 181  F  I  A  F  S   Q  I  P  E  L    A  K  R  I  K    M  F  A  L
 601 GGTCCTGTGGCTTCC GTCGCCTTCTGTACT AGCCCTATGGCCAAA TTAGGACGATTACCA
 201  G  P  V  A  S   V  A  F  C  T    S  P  M  A  K    L  G  R  L  P
 661 GATCATCTCATTAAG GACTTATTTGGAGAC AAAGAATTTCTTCCC CAGAGTGCGTTTTTG
 221  D  H  L  I  K   D  L  F  G  D    K  E  F  L  P    Q  S  A  F  L
 721 AAGTGGCTGGGTACC CACGTTTGCACTCAT GTCATACTGAAGGAG CTCTGTGGAAATCTC
 241  K  W  L  G  T   H  V  C  T  H    V  I  L  K  E    L  C  G  N  L
 781 TGTTTTCTTCTGTGT GGATTAATGAGAGA AATTTAAATATGTCT AGAGTGGATGTATAT
 261  C  F  L  L  C   G  F  N  E  R    N  L  N  M  S    R  V  D  V  Y
 841 ACAACACATTCTCCT GCTGGAACTTCTGTG CAAAACATGTTACAC TGGAGCCAGGCTGTT
 281  T  T  H  S  P   A  G  T  S  V    Q  N  M  L  H    W  S  Q  A  V
 901 AAATTCCAAAAGTTT CAAGCCTTTGACTGG GGAAGCAGTGCCAAG AATTATTTTCATTAC
 301  K  F  Q  K  F   Q  A  F  D  W    G  S  S  A  K    N  Y  F  H  Y
 961 AACCAGAGTTATCCT CCCACATACAATGTG AAGGACATGCTTGTG CCGACTGCAGTCTGG
 321  N  Q  S  Y  P   P  T  Y  N  V    K  D  M  L  V    P  T  A  V  W
1021 AGCGGGGGTCACGAC TGGCTTGCAGATGTC TACGACGTCAATATC TTACTGACTCAGATC
 341  S  G  G  H  D   W  L  A  D  V    Y  D  V  N  I    L  L  T  Q  I
1081 ACCAACTTGGTGTTC CATGAGAGCATTCCG GAATGGGAGCATCTT GACTTCATTTGGGGC
 361  T  N  L  V  F   H  E  S  I  P    E  W  E  H  L    D  F  I  W  G
1141 CTGGATGCCCCTTGG AGGCTTTATAATAAA ATTATTAATCTAATG AGGAAATATCAGTGA
 381  L  D  A  P  W   R  L  Y  N  K    I  I  N  L  M    R  K  Y  Q  M
```

Figure 1

Rank Order Based on Intracellular Lipase Activity
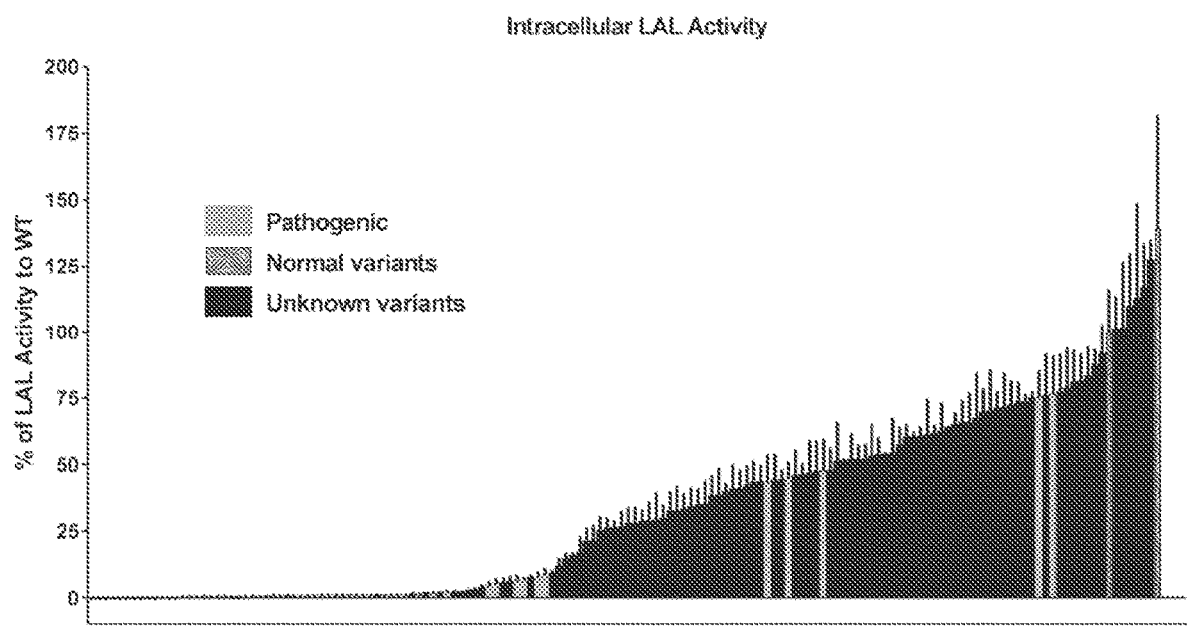
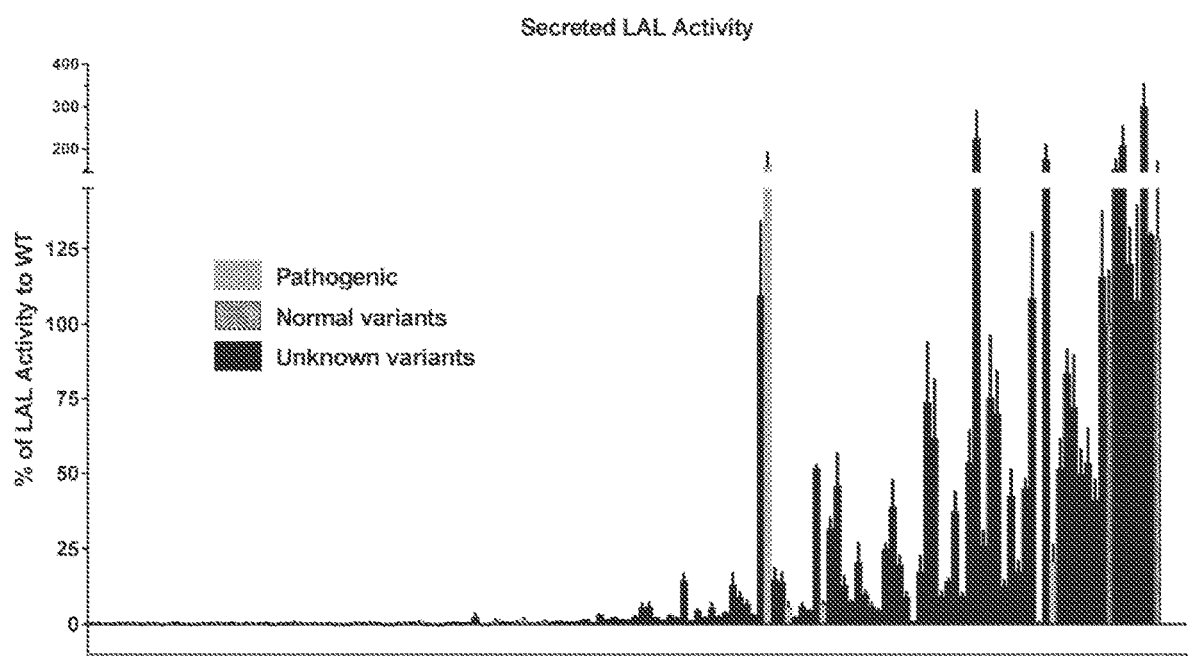
Figure 2

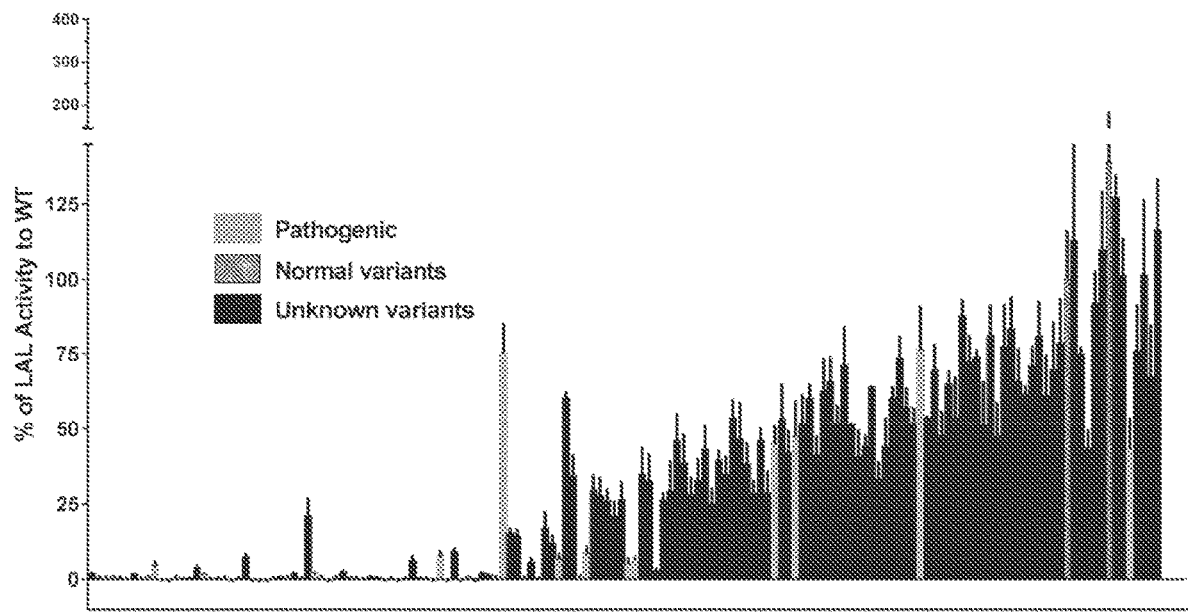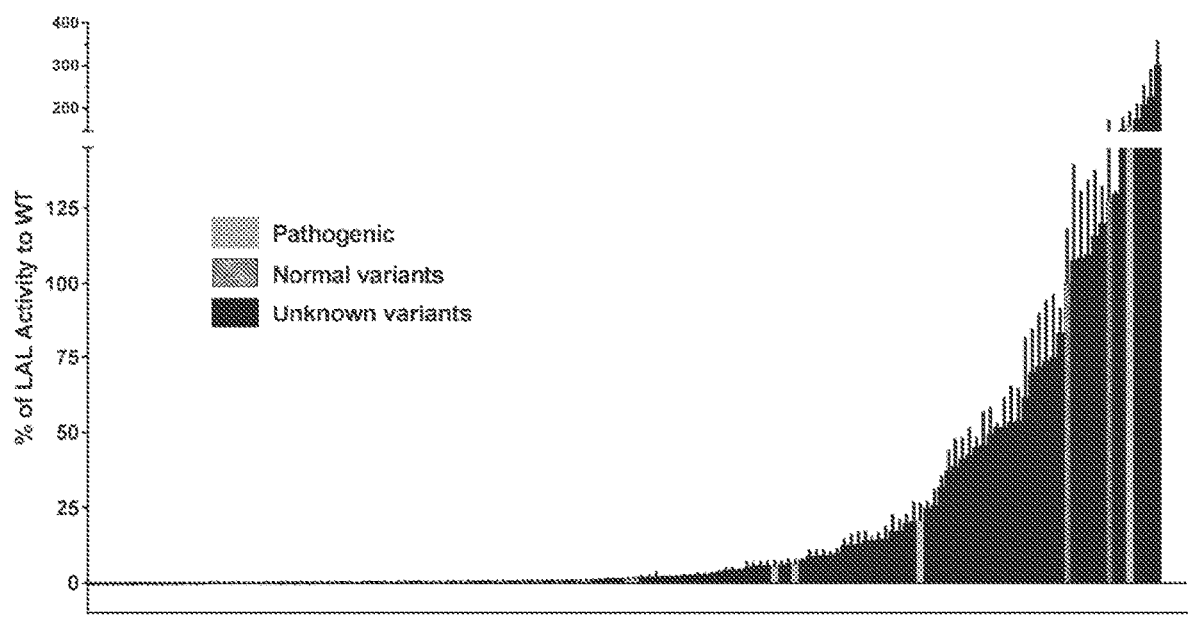
Figure 3

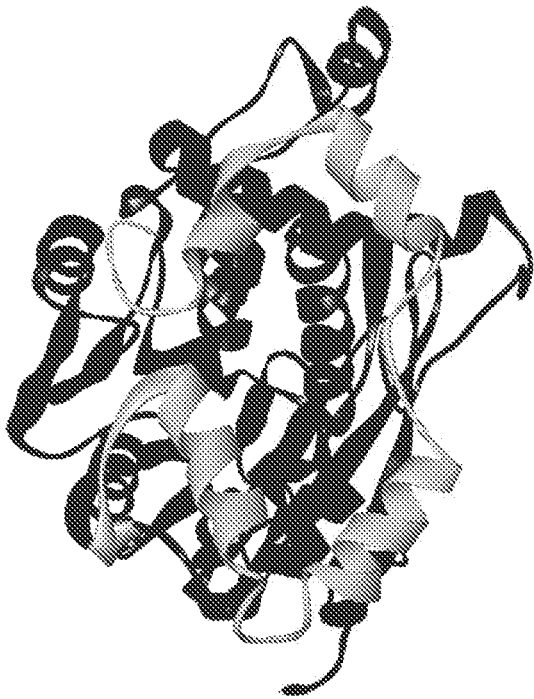
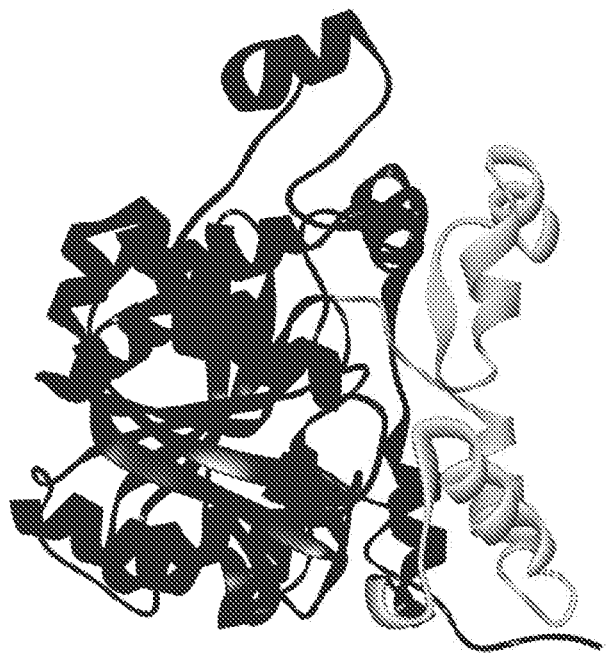
Figure 4A

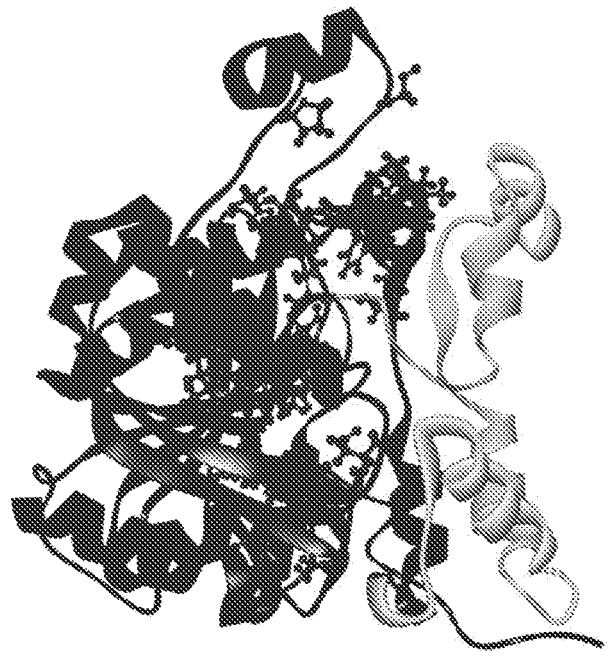
Figure 4B

Known pathogenic variants with >10% LAL activity
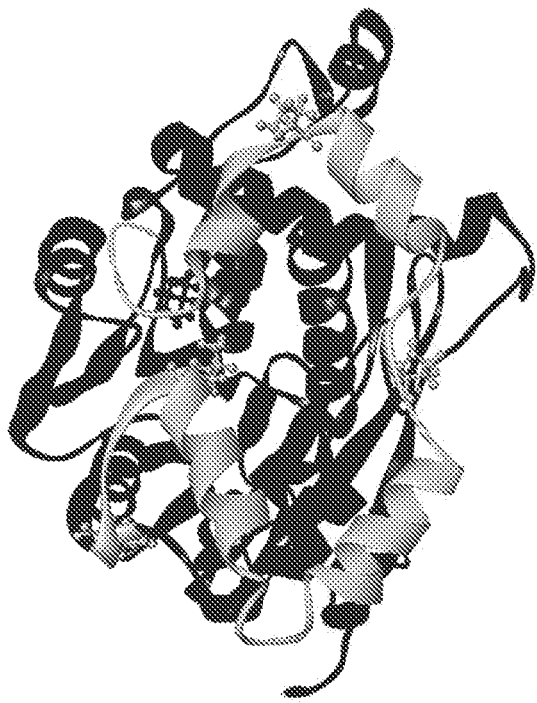
Front view
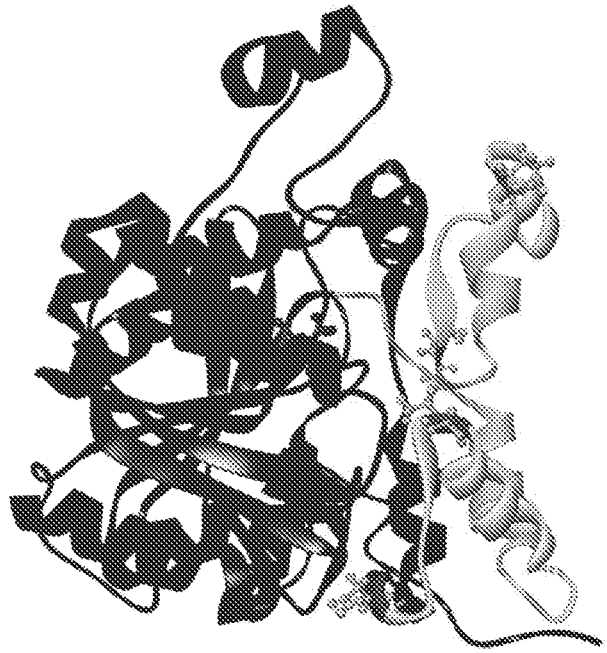
Bottom view
Figure 4C

SEQUENCE LISTING

<160> NUMBER OF SEQ ID NOS: 3

<210> SEQ ID NO 1
<211> LENGTH: 1200
<212> TYPE: DNA
<213> ORGANISM: Human

<400> SEQUENCE: 1

| | | | | | |
|---|---|---|---|---|---|
| atgaaaatgc | ggttcttggg | gttggtggtc | tgtttggttc | tctggaccct | gcattctgag | 60 |
| gggtctggag | ggaaactgac | agctgtggat | cctgaaacaa | acatgaatgt | gagtgaaatt | 120 |
| atctcttact | ggggattccc | tagtgaggaa | tacctagttg | agacagaaga | tggatatatt | 180 |
| ctgtgcctta | accgaattcc | tcatgggagg | aagaaccatt | ctgacaaagg | tcccaaacca | 240 |
| gttgtcttcc | tgcaacatgg | cttgctggca | gattctagta | actgggtcac | aaaccttgcc | 300 |
| aacagcagcc | tgggcttcat | tcttgctgat | gctggttttg | acgtgtggat | gggcaacagc | 360 |
| agaggaaata | cctggtctcg | gaaacataag | acactctcag | tttctcagga | tgaattctgg | 420 |
| gctttcagtt | atgatgagat | ggcaaaatat | gacctaccag | cttccattaa | cttcattctg | 480 |
| aataaaactg | gccaagaaca | agtgtattat | gtgggtcatt | ctcaaggcac | cactataggt | 540 |
| tttatagcat | tttcacagat | ccctgagctg | gctaaaagga | ttaaaatgtt | ttttgccctg | 600 |
| ggtcctgtgg | cttccgtcgc | cttctgtact | agccctatgg | ccaaattagg | acgattacca | 660 |
| gatcatctca | ttaaggactt | atttggagac | aaagaatttc | ttccccagag | tgcgtttttg | 720 |
| aagtggctgg | gtacccacgt | ttgcactcat | gtcatactga | aggagctctg | tggaaatctc | 780 |
| tgttttcttc | tgtgtggatt | taatgagaga | aatttaaata | tgtctagagt | ggatgtatat | 840 |
| acaacacatt | ctcctgctgg | aacttctgtg | caaaacatgt | tacactggag | ccaggctgtt | 900 |
| aaattccaaa | agtttcaagc | ctttgactgg | ggaagcagtg | ccaagaatta | ttttcattac | 960 |
| aaccagagtt | atcctcccac | atacaatgtg | aaggacatgc | ttgtgccgac | tgcagtctgg | 1020 |
| agcgggggtc | acgactggct | tgcagatgtc | tacgacgtca | atatcttact | gactcagatc | 1080 |
| accaacttgg | tgttccatga | gagcattccg | gaatgggagc | atcttgactt | catttggggc | 1140 |
| ctggatgccc | cttggaggct | ttataataaa | attattaatc | taatgaggaa | atatcagtga | 1200 |

<210> SEQ ID NO 2
<211> LENGTH: 399
<212> TYPE: PRT
<213> ORGANISM: Human

<400> SEQUENCE: 2

Met Lys Met Arg Phe Leu Gly Leu Val Val Cys Leu Val Leu Trp Thr
1               5                   10                  15

Leu His Ser Glu Gly Ser Gly Gly Lys Leu Thr Ala Val Asp Pro Glu
            20                  25                  30

Thr Asn Met Asn Val Ser Glu Ile Ile Ser Tyr Trp Gly Phe Pro Ser
        35                  40                  45

Glu Glu Tyr Leu Val Glu Thr Glu Asp Gly Tyr Ile Leu Cys Leu Asn
    50                  55                  60

Arg Ile Pro His Gly Arg Lys Asn His Ser Asp Lys Gly Pro Lys Pro
65                  70                  75                  80

Val Val Phe Leu Gln His Gly Leu Leu Ala Asp Ser Ser Asn Trp Val
                85                  90                  95

Thr Asn Leu Ala Asn Ser Ser Leu Gly Phe Ile Leu Ala Asp Ala Gly
            100                 105                 110

```
Phe Asp Val Trp Met Gly Asn Ser Arg Gly Asn Thr Trp Ser Arg Lys
        115                 120                 125

His Lys Thr Leu Ser Val Ser Gln Asp Glu Phe Trp Ala Phe Ser Tyr
    130                 135                 140

Asp Glu Met Ala Lys Tyr Asp Leu Pro Ala Ser Ile Asn Phe Ile Leu
145                 150                 155                 160

Asn Lys Thr Gly Gln Glu Gln Val Tyr Tyr Val Gly His Ser Gln Gly
                165                 170                 175

Thr Thr Ile Gly Phe Ile Ala Phe Ser Gln Ile Pro Glu Leu Ala Lys
            180                 185                 190

Arg Ile Lys Met Phe Phe Ala Leu Gly Pro Val Ala Ser Val Ala Phe
        195                 200                 205

Cys Thr Ser Pro Met Ala Lys Leu Gly Arg Leu Pro Asp His Leu Ile
    210                 215                 220

Lys Asp Leu Phe Gly Asp Lys Glu Phe Leu Pro Gln Ser Ala Phe Leu
225                 230                 235                 240

Lys Trp Leu Gly Thr His Val Cys Thr His Val Ile Leu Lys Glu Leu
                245                 250                 255

Cys Gly Asn Leu Cys Phe Leu Leu Cys Gly Phe Asn Glu Arg Asn Leu
            260                 265                 270

Asn Met Ser Arg Val Asp Val Tyr Thr Thr His Ser Pro Ala Gly Thr
        275                 280                 285

Ser Val Gln Asn Met Leu His Trp Ser Gln Ala Val Lys Phe Gln Lys
    290                 295                 300

Phe Gln Ala Phe Asp Trp Gly Ser Ser Ala Lys Asn Tyr Phe His Tyr
305                 310                 315                 320

Asn Gln Ser Tyr Pro Pro Thr Tyr Asn Val Lys Asp Met Leu Val Pro
                325                 330                 335

Thr Ala Val Trp Ser Gly His Asp Trp Leu Ala Asp Val Tyr Asp
        340                 345                 350

Val Asn Ile Leu Leu Thr Gln Ile Thr Asn Leu Val Phe His Glu Ser
        355                 360                 365

Ile Pro Glu Trp Glu His Leu Asp Phe Ile Trp Gly Leu Asp Ala Pro
    370                 375                 380

Trp Arg Leu Tyr Asn Lys Ile Ile Asn Leu Met Arg Lys Tyr Gln
385                 390                 395

<210> SEQ ID NO 3
<211> LENGTH: 21
<212> TYPE: PRT
<213> ORGANISM: Human

<400> SEQUENCE: 3

Met Lys Met Arg Phe Leu Gly Leu Val Val Cys Leu Val Leu Trp Thr
1               5                   10                  15

Leu His Ser Glu Gly
            20
```

LYSOSOMAL ACID LIPASE DEFICIENCY COMPOSITIONS AND METHODS

This application is the § 371 U.S. National Stage of International Application No. PCT/US17/37928, filed Jun. 16, 2017, which claims the benefit of U.S. Provisional Patent Applications Ser. No. 62/351,631, filed Jun. 17, 2016; Ser. No. 62/358,951, filed Jul. 6, 2016, and Ser. No. 62/457,356, filed Feb. 10, 2017, the disclosures of which are incorporated herein by reference in their entireties.

SEQUENCE LISTING

This application contains a Sequence Listing electronically submitted via EFS-Web to the United States Patent and Trademark Office as an ASCII text file entitled "535-0001_ST25.txt" having a size of 6 kilobytes and created on Jun. 5, 2017. The information contained in the Sequence Listing is incorporated by reference herein.

BACKGROUND

Lysosomal Acid Lipase Deficiency (LAL-D, also known as LALD) is a genetic disease which is characterized by abnormal lipid accumulation in many parts of the body due to a marked decrease in activity of the enzyme lysosomal acid lipase (LAL). LAL is encoded by the LIPA gene. Although a single disease, LAL-D presents with two major forms: early onset and late onset. Early onset LAL-D, also known as Wolman Disease, is characterized by severe malabsorption, growth failure, and hepatic failure and is usually fatal within the first year of life. The late onset form of the disease, also known as Cholesteryl Ester Storage Disease (CESD), occurs in both children and adults and is an under-appreciated cause of fatty liver with prominent microvesicular steatosis and cirrhosis. Although the natural history of the disease has not been well studied, serious liver complications are frequently described including early death and liver transplantation. Other complications can include premature atherosclerosis (hardening of arteries) associated with high levels of total cholesterol and low-density lipoprotein (LDL) cholesterol, often called the "bad" cholesterol. The levels of triglycerides can also be high and the levels of high-density lipoprotein (HDL) cholesterol (the "good" cholesterol) are typically low.

LAL-D may be suspected in patients that exhibit hepatomegaly, elevated transaminases, and/or a serum lipid profile that is characterized by high total serum concentrations of cholesterol, low-density lipoprotein, and triglycerides; and low serum concentration of high-density lipoprotein. A diagnosis of LAL-D can be established through genetic testing that reveals either biallelic pathogenic variants in the LIPA gene or by a finding of deficient LAL enzyme activity in peripheral blood leukocytes, fibroblasts, or dried blood spots. See Hoffman et al. Lysosomal Acid Lipase Deficiency. 2015 Jul. 30. In: Pagon et al., editors. GeneReviews® [Internet]. Seattle (Wash.): University of Washington, Seattle; 1993-2016. Available from: http://www.ncbi.nlm.nih.gov/books/NBK305870/.

The prevalence of LAL-D has been estimated at 1 in 130,000 within Caucasian and Hispanic populations. This is based on the assumption that 60% of these patients harbor the c.894G>A LIPA mutation (the gene that encodes LAL) (Scott et al., Hepatology, 2013, 58(3), 958-65; Epub 2013 Jul. 29). The mutation at c.894G>A is the most common pathogenic variant resulting in CESD, and involves a G-to-A transition at the last base of exon 8, thereby disrupting the normal donor splice consensus sequence. Typically, this results in alternative splicing and subsequent skipping of exon 8. Approximately 3%-5% of transcripts are correctly spliced, however, allowing for residual enzyme activity. Hoffman et al. Lysosomal Acid Lipase Deficiency. 2015 Jul. 30. In: Pagon et al., editors. GeneReviews® [Internet]. Seattle (Wash.): University of Washington, Seattle; 1993-2016. Available from: http://www.ncbi.nlm.nih.gov/books/NBK305870/. The prevalence of LAL-D outside of the Caucasian and Hispanic population groups is not well defined given that c.894G>A mutation is rarely found in non-Caucasian and non-Hispanic LAL-D patients.

SUMMARY OF THE INVENTION

In one aspect, the invention describes mutations in the nucleotide sequence of a human LIPA gene that have been discovered to be associated with reduced lysosomal acid lipase (LAL) activity. These mutations may be referred to herein as "LAL activity-reducing mutations." In some embodiments, the activity of the LAL encoded by the mutated gene is reduced so far that it is no longer detectable or is eliminated. In other embodiments, the activity of the LAL encoded by the mutated gene is reduced but still detectable. In some embodiments, the LAL-activity reducing mutation is present in the coding region of a human LIPA gene. A human LIPA gene that is mutated such that it produces a LAL with reduced activity is suspected of being pathogenic and as such, is referred to herein as a potentially pathogenic LIPA gene variant or allelic variant. In some embodiments, the mutation results in an amino acid substitution in the LAL encoded by the mutated LIPA gene. In some embodiments, the mutation causes a truncation of LAL. The mutation can be, for example, a missense mutation or a nonsense mutation. In some embodiments, the mutation causes misregulation of precursor RNA splicing, and/or alternative precursor mRNA splicing. In some embodiments, the mutation can be an insertion or deletion of one or more amino acids, and optionally can cause a frameshift in the LAL encoded by the mutated LIPA gene. One or more of the LAL activity-reducing mutations described herein may occur alone, or in combination with each other and/or in combination with one or more known mutations in the human LIPA gene.

In another aspect, the invention describes thirteen additional novel clinically identified mutations in the nucleotide sequence of a human LIPA gene. These additional mutations were discovered in combination with known pathogenic LIPA mutations. A human LIPA gene that includes one or more of these thirteen novel mutations is suspected of being pathogenic and as such, is also referred to herein as a potentially pathogenic LIPA gene variant.

In another aspect, the invention provides a method for detecting the presence or absence of an LAL activity-reducing mutation in the nucleotide sequence of a LIPA gene of a human subject. This method makes possible a determination as to whether the subject possesses a potentially pathogenic LIPA gene variant, also referred to as a potentially pathogenic LIPA allele or allelic variant. The presence of a potentially pathogenic gene variant may be indicative of LAL-D. Any convenient detection method can be used to detect an LAL activity-reducing mutation.

In another aspect, the invention provides a method for detecting the presence or absence of a novel clinically identified mutation, as described herein, in the nucleotide sequence of a LIPA gene of a human subject. This method makes possible a determination as to whether the subject possesses a potentially pathogenic LIPA gene variant, also referred to as a potentially pathogenic LIPA allele or allelic variant. The presence of a potentially pathogenic gene variant may be indicative of LAL-D. Any convenient detection method can be used to detect a novel clinically identified mutation.

In another aspect, the invention provides a method for diagnosing Lysosomal Acid Lipase Deficiency (LAL-D) in a human subject. The nucleotide sequence of the LIPA gene of the subject, or related mRNA or cDNA, is analyzed to determine the presence of a mutation associated with reduced LAL activity, wherein reduced LAL activity of the gene variant is indicative of LAL-D. Additionally or alternatively, the nucleotide sequence is analyzed to determine the presence of a novel clinically identified mutation, as described herein. Mutation detection can be used alone in combination with other diagnostic factors. The diagnostic method of the invention optionally includes treating the patient for LAL-D.

In some embodiments of the detection or diagnostic method, the LIPA gene is present in or isolated from a biological sample obtained from a human subject. The subject can be a child or an adult. The polynucleotide evaluated for presence or absence of the mutation can be, for example, DNA, RNA or cDNA. In some embodiments of the detection or diagnostic method, genetic analysis for the presence or absence of a mutation takes the form of exomic or genomic analysis performed on nucleic acids obtained from the subject.

In another aspect, the invention provides a kit for detecting an LAL activity-reducing mutation and/or a novel clinically identified mutation in the nucleotide sequence of a LIPA gene. In some embodiments, the kit includes at least one oligonucleotide primer specific for an LAL activity-reducing LIPA gene mutation or a novel clinically identified LIPA gene mutation as described herein, and instructions relating to detecting mutations in the nucleotide sequence of a LIPA gene. In some embodiments, the kit includes at least one allele-specific oligonucleotide probe for an LAL activity-reducing LIPA gene mutation or the novel clinically identified LIPA gene mutation as described herein and instructions relating to detecting mutations in the nucleotide sequence of a LIPA gene. Optionally the kit includes a multiplicity of primers or probes to permit the detection of a multiplicity of mutations in the nucleotide sequence of a human LIPA gene, thereby increasing the diagnostic or screening efficiency of the kit.

In another aspect, the invention provides a method for treating a patient afflicted with, or suspected of being afflicted with, LAL-D, wherein the nucleotide sequence of a LIPA gene of the patent contains an LAL activity-reducing mutation and/or a novel clinically identified mutation as described herein. In some embodiments, the patient is treated with enzyme replacement therapy, for example by using recombinant LAL. In some embodiments, the patient is treated with therapeutic polynucleotides. Exemplary treatments and therapeutic agents for use with LAL-D patients are described, without limitation, in US2016/0051638; US2012/0064055; US 2014/0348752; US 2014/0155475 (therapeutic polynucleotides); WO/2012/050695; WO/2012/112681; WO/2012/112677; and WO/2011/133960.

Definitions

For convenience, certain terms employed in the specification, examples, and appended claims are set forth herein to illustrate and define the meaning and scope of the various terms used to describe the present invention.

"LAL" as used herein refers to "lysosomal acid lipase," and the two terms are used interchangeably throughout the specification. The LAL can be a human protein, i.e., human lysosomal acid lipase. An exemplary recombinant human LAL is sebelipase alfa, which is available under the tradename KANUMA (Kanuma®) from Alexion Pharmaceuticals, Inc. LAL is also referred to in the literature as acid cholesteryl ester hydrolase, cholesteryl esterase, Lipase A, LIPA, and sterol esterase.

LAL is encoded by the LIPA gene, which is present in the human population in a variety of allelic forms. The most prevalent allele, referred to herein as "wild-type" (WT), encodes a functional ("wild-type") LAL. Wild-type LAL is referred to herein as having "normal" activity. The coding sequence of a wild-type human LIPA gene (SEQ ID NO:1) and the amino acid sequence of a wild-type LAL (SEQ ID NO:2) are shown in FIG. 1.

LAL catalyzes the hydrolysis of cholesterol esters and triglycerides to free cholesterol, glycerol, and free fatty acids. Thus, "LAL activity" can be measured, for example, by the cleavage of the fluorogenic substrate, 4-methylumbelliferyl oleate (4MUO). Cleavage of 4MUO can be detected, for example, by excitation at about 360 nm and emission at 460 nm of the released fluorophore, 4-methylumbelliferone (4-MU). Results can be reported in relative fluorescence units (RFU). For example, the amount of substrate cleaved in a 30 minute endpoint assay can be quantified relative to a 4-MU standard curve, and one unit (U) of activity can be defined as the amount of enzyme required to cleave 1 micromole of 4MUO per minute at 37° C. Accordingly, functional fragments or variants of LAL include fragments or variants that have LAL activity, e.g., the ability to hydrolyze cholesterol esters and/or triglycerides.

As used herein "exogenous LAL" refers to LAL that is not naturally produced by a patient. For example, exogenous LAL includes recombinant LAL protein that is administered to a patient, LAL protein that is isolated from a person or animal and administered to a patient, and LAL protein that is produced (i.e., expressed) in a patient as a result of administration of LAL-encoding RNA and/or DNA or another treatment that increases expression of endogenous LAL protein.

"Intravenous injection," often medically referred to as IV push or bolus injection, refers to a route of administration in which a syringe is connected to the IV access device and the medication is injected directly, typically rapidly and occasionally up to a period of 15 minutes if it might cause irritation of the vein or a too-rapid effect. Once a medicine has been injected into the fluid stream of the IV tubing, there must be some means of ensuring that it gets from the tubing to the patient. Usually this is accomplished by allowing the fluid stream to flow normally and thereby carry the medicine into the bloodstream. However, in some cases a second fluid injection, sometimes called a "flush," is used following the first injection to facilitate the entering of the medicine into the bloodstream.

"Intravenous infusion" refers to a route of administration in which medication is delivered over an extended period of time. For example, the medication can be delivered to a patient over a period of time between 1 and 8 hours. The medication can also be delivered to a patient over a period of about 1, about 2, about 3, about 4, about 5, about 6, about 7, or about 8 hours. To accomplish an intravenous infusion, an IV gravity drip or an IV pump can be used. IV infusion is typically used when a patient requires medications only at certain times and does not require additional intravenous fluids (e.g., water solutions which can contain sodium, chloride, glucose, or any combination thereof) such as those that restore electrolytes, blood sugar, and water loss.

The term "patient" as used herein refers to any person receiving or who has received or is to receive medical care or treatment, e.g., as directed by a medical care provider.

A "therapeutically effective" amount or a "therapeutically effective" dose, as the terms are used herein, refers to the amount or the dose (e.g., amount and/or interval) of drug required to produce an intended therapeutic response. A therapeutically effective dose refers to a dose that, as compared to a corresponding subject who has not received such a dose, results in improved treatment, healing, prevention, or amelioration of a disease, disorder, or side effect, or a decrease in the rate of the occurrence or advancement of a disease or disorder. The term also includes within its scope, doses effective to enhance physiological functions.

The terms "treat," "treating," and "treatment" refer to methods of alleviating, abating, or ameliorating a disease or symptom, preventing an additional symptom, ameliorating or preventing an underlying cause of a symptom, inhibiting a disease or condition, arresting the development of a disease or condition, relieving a disease or condition, causing regression of a disease or condition, relieving a condition caused by the disease or condition, or stopping a symptom of the disease or condition either prophylactically and/or after the symptom has occurred.

As used herein with reference to a particular dose, "$kg^{-1}$", "per kg", "/kg," and "per kilogram" represent "per kilogram of body weight" of the mammal, and thus the terms can be used interchangeably.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "proteins," "amino acid chains," or any other term used to refer to a chain or chains of two or more amino acids, are included within the definition of "polypeptide," and the term "polypeptide" may be used instead of, or interchangeably with any of these terms. The term "polypeptide" is also intended to be inclusive of the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

Other polypeptides disclosed herein are fragments, derivatives, analogs, or variants of the foregoing polypeptides, and any combination thereof. The terms "fragment," "variant," "derivative" and "analog" when referring to any of the polypeptides disclosed herein include any polypeptides which retain at least some of the activity of the corresponding native polypeptide (e.g., LAL polypeptide fragments, variants, derivatives, and analogs that retain the ability to hydrolyze cholesterol esters and/or triglycerides). Fragments of polypeptides include, for example, proteolytic fragments, as well as deletion fragments. Variants of a polypeptide include fragments as described above, and also polypeptides with altered amino acid sequences due to amino acid substitutions, deletions, or insertions. Variants can occur naturally or be non-naturally occurring. Non-naturally occurring variants can be produced using art-known mutagenesis techniques. Variant polypeptides can comprise conservative or non-conservative amino acid substitutions, deletions, or additions. Derivatives are polypeptides which have been altered so as to exhibit additional features not found on the native polypeptide. Examples include fusion proteins. Variant polypeptides can also be referred to herein as "polypeptide analogs." As used herein, a "derivative" of a subject polypeptide can contain one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and/or ornithine can be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. An "isolated" nucleic acid or polynucleotide is one that has been removed from its native environment. For example, a recombinant polynucleotide encoding LAL contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can be or can include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector can contain a single coding region, or can comprise two or more coding regions. In addition, a vector, polynucleotide, or nucleic acid of the invention can encode heterologous coding regions, either fused or unfused to a nucleic acid encoding a LAL polypeptide or fragment, variant, or derivative thereof. Heterologous coding regions include without limitation specialized elements or motifs, such as a secretory signal peptide or a heterologous functional domain.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., the MKMRFLGLVVCLVLWTLHSEG (SEQ ID NO:3) signal peptide of human LAL is used, or a functional derivative of that sequence that retains the ability to direct the secretion of the polypeptide that is operably associated with it. Alternatively, a heterologous signal peptide (e.g., a heterologous mammalian or avian signal peptide), or a functional derivative thereof, may be used. For example, the wild-type leader sequence may be substituted with the leader sequence of human tissue plasminogen activator (TPA) or mouse β-glucuronidase.

"Vector" means a polynucleotide comprised of single strand, double strand, circular, or supercoiled DNA or RNA. A typical vector can be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements can be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites. An intron optionally can be included in the construct, for example, 5' to the coding sequence. A vector is constructed so that the particular coding sequence is located in the vector with the appropriate regulatory sequences, the positioning and orientation of the coding sequence with respect to the control sequences being such that the coding sequence is transcribed under the "control" of the control or regulatory sequences. Modification of the sequences encoding the particular protein of interest can be desirable to achieve this end. For example, in some cases it can be necessary to modify the sequence so that it can be attached to the control sequences with the appropriate orientation, or to maintain the reading frame. The control sequences and other regulatory sequences can be ligated to the coding sequence prior to insertion into a vector. Alternatively, the coding sequence can be cloned directly into an expression vector which already contains the control sequences and an appropriate restriction site which is in reading frame with and under regulatory control of the control sequences.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, "host cells" refers to cells that harbor vectors constructed using recombinant DNA techniques and encoding at least one heterologous gene.

As used herein, the term "pharmaceutical composition" refers to a mixture of a compound described herein with other chemical components, such as carriers, stabilizers, diluents, dispersing agents, suspending agents, thickening agents, and/or excipients.

The words "preferred" and "preferably" refer to embodiments of the invention that may afford certain benefits, under certain circumstances. However, other embodiments may also be preferred, under the same or other circumstances, whether described as such or not herein. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

All headings are for the convenience of the reader and should not be used to limit the meaning of the text that follows the heading, unless so specified.

The above summary of the invention is not intended to describe each disclosed embodiment or every implementation of the invention. The description that follows more particularly exemplifies illustrative embodiments. In several places throughout the application, guidance may be provided through lists of examples, which examples can be used in various combinations. In each instance, the recited list serves only as a representative group and should not be interpreted as an exclusive list.

DESCRIPTION OF THE FIGURES

FIG. 1 shows the nucleotide sequence of the coding region of the wild-type human LIPA gene (SEQ ID NO:1) and the amino acid sequence of the encoded lysosomal acid lipase (LAL) (SEQ ID NO:2) obtained from the NCBI CCDS Database, CCDS7401.1; see also NCBI Gene ID 3988; NCBI Reference Sequence: NM_001127605.2; NCBI Reference Sequence: NP_001121077.1; and NCBI Reference Sequence: NM_000235.3 for additional LIPA nucleotide sequence information.

FIG. 2 shows rank order based on intracellular lipase activity. The enzymes are ordered on the x-axis from lowest to highest based on intracellular lipase activity. The top panel shows intracellular LAL activity on the y-axis. The bottom panel shows secreted LAL activity on the y-axis.

FIG. 3 shows rank order based on secreted lipase activity. The enzymes are ordered on the x-axis from lowest to highest based on secreted lipase activity. The top panel shows intracellular LAL activity on the y-axis. The bottom panel shows secreted LAL activity on the y-axis.

FIG. 4A shows ribbon drawings, front and bottom views, of a homology modeled human LAL derived from canine gastric lipase PDB: 1K8Q (Roussel et al., 1999, J. Biol. Chem. 274(24):16995-17002). Black=catalytic domain; gray=lid domain (residues 206-271).

FIG. 4B shows front and bottom views of the homology model as in FIG. 4A, annotated to show missense mutations for known pathogenic variants with <10% LAL activity; ball and stick=residue positions at which mutations are known to cause LAL-D.

FIG. 4C shows front and bottom views of the homology model as in FIG. 4A, annotated to show missense mutations for known pathogenic variants with >10% LAL activity; ball and stick=residue positions at which mutations are known to cause LAL-D.

ILLUSTRATIVE DESCRIPTION OF THE INVENTION

Figure 5:
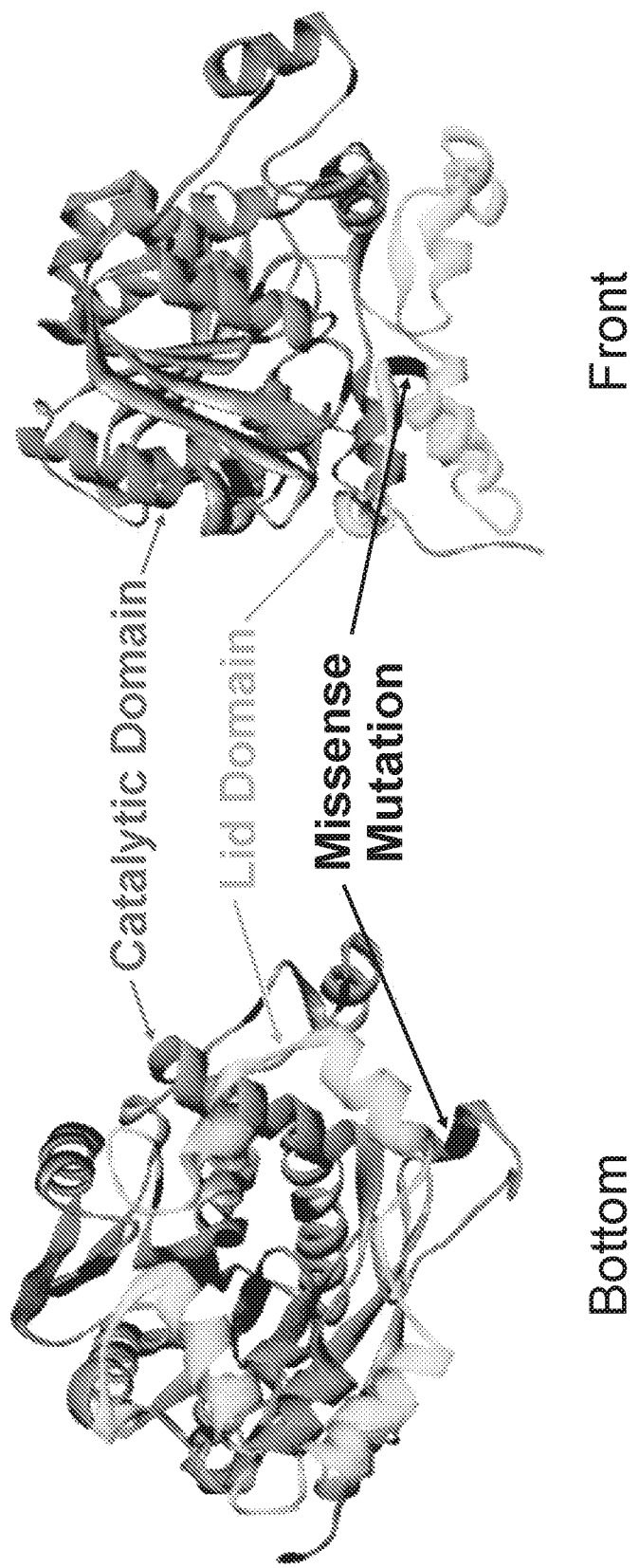
FIG. 5 shows a homology model of human LAL derived from canine LAL PDB: 1K8Q (see, Roussel A, Miled N, Berti-Dupuis L, et al. J Biol Chem. 2002; 277(3):2266-2274); selected missense mutation locations are in black, the catalytic domain is in dark gray, and the lid domain is in light gray.

This disclosure describes mutations in the nucleotide sequence of a human LIPA gene that have been discovered to be associated with reduced lysosomal acid lipase (LAL) activity. LAL activity-reducing mutations are of clinical and research interest because reduced LAL activity is a marker for Lysosomal Acid Lipase Deficiency (LAL-D). It is expected that the identification of LAL activity-reducing mutations in the human LIPA gene as set forth herein will be of important medical significance in that it will improve genetic screening for human subjects suspected of having LAL-D.

In one aspect, the invention provides a method for detecting a potentially pathogenic mutation in a human LIPA nucleotide sequence. The detection method includes providing a biological sample that includes a nucleic acid; and performing a genetic analysis on the biological sample to detect the presence of a potentially pathogenic mutation in a human LIPA nucleotide sequence. Optionally, the detection method includes diagnosing a patient with lysosomal acid lipase deficiency (LAL-D) when the presence of a potentially pathogenic mutation in the LIPA nucleotide sequence of the patient is detected. The biological sample can be obtained from a pediatric or adult patient. The patient may be suspected of being afflicted with, or may be afflicted with, with Wolman Disease or Cholesteryl Ester Storage Disease (CESD). The method may further include administering a therapeutically effective amount of a recombinant human LAL to the patient.

In another aspect, the invention provides a method for diagnosing lysosomal acid lipase deficiency (LAL-D) in a patient. The diagnostic method includes providing a biological sample from a patient, wherein the sample includes a nucleic acid; performing a genetic analysis on the biological sample to detect the presence of a potentially pathogenic mutation in a human LIPA nucleotide sequence; and diagnosing the patient with LAL-D when the presence of a potentially pathogenic mutation in the LIPA nucleotide sequence of the subject is detected.

In another aspect, the invention provides a method for treating a patient afflicted with or suspected of being afflicted with LAL-D. The method includes administering a therapeutically effective amount of a recombinant human LAL to the patient who has been determined to possess at least one LIPA allelic variant that includes a potentially pathogenic mutation as described herein.

The recombinant human LAL administered to a patient may include sebelipase alfa.

In some aspects, the potential pathogenicity of a LIPA gene variant can be evaluated using in silico techniques. One or more in silico prediction methods, such as Mutation-Taster, PolyPhen2, SIFT, and/or Provean, are utilized to assess the severity of missense mutations and to predict the impact of the mutation on LAL enzymatic activity. Missense mutations can be identified based on a unanimous score, or on a consensus score, of two, three, four or more in silico methods. For example, a mutation can be identified as "deleterious" if four methods predict it to be "deleterious."

The invention includes a method for detecting the presence or absence of an LAL activity-reducing mutation or a novel clinically identified mutation in the nucleotide sequence of a LIPA gene of a human subject. Any one or more of the LAL activity-reducing mutations or the novel clinically identified mutations described herein can be detected. The presence of one or more LIPA alleles possessing an LAL activity-reducing mutation or clinically identified mutation as described herein (i.e., one or more potentially pathogenic LIPA gene variants) has clinical relevance to the diagnosis of LAL-D.

Detection of a mutation in the nucleotide sequence of a LIPA gene can be accomplished using any convenient method. Many techniques for genetic testing and genetic analysis are known to the art. Genetic analysis for the presence of a potentially pathogenic LIPA gene variant in a subject can be carried out, for example, using recently developed nucleotide sequencing technologies or using traditional hybridization technologies. For example, the analysis can be carried out using positional cloning based on linkage analysis and/or Sanger sequencing. Another option is RNA whole transcriptome sequencing, which may also be referred to as RNA sequencing, RNA-seq or whole transcriptome shotgun sequencing (WTSS), which typically utilizes next-generation sequencing technologies (NGS) and focuses on a gene expression profile, is able to detect alternative splicing events, and can detect single nucleotide variants. Another option is exome sequencing or whole exome sequencing (WES or WXS), wherein some or all of the expressed genes in a genome (i.e., the exome) are sequenced. Whole-exome sequencing facilitates identification of autosomal recessive disease genes in single patients from non-consanguineous families. Another option is whole-genome sequencing (WGS) which provides a complete view of the human genome, including point mutations in distant enhancers and other regulatory elements. Pabinger et al., Brief. Bioinform (2014) 15(2):256-278, Epub Jan. 21, 2013. Other exemplary methods of genetic analysis include, but are not limited to, restriction fragment length polymorphism identification (RFLPI) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads. It should be understood that mutation analysis and detection techniques are rapidly evolving and detection of a potentially pathogenic LIPA gene variant is not limited to any particular detection technique.

Mutations in the nucleotide sequence of a LIPA gene can be detected by analyzing any polynucleotide or polynucleotide fragment that derives from, directly or indirectly the LIPA gene of a subject. Types of polynucleotides that can be analyzed for mutations include, without limitation, genomic DNA (whole or partial), exomic RNA (whole or partial), primary RNA transcripts such as precursor RNA, processed RNA such as spliced mRNA, mature RNA and mRNA, and cDNA. The nucleotide sequence to be analyzed typically includes coding sequences, for example exon sequences, and may also include intron sequences, particularly intron sequences that proximal to splice junctions and may thus affect production of the mature mRNA and/or protein translation and structure.

The nucleic acids (e.g., DNA or RNA) to be analyzed for presence of one or more LAL activity-reducing and/or novel clinically identified gene mutations can be present in or isolated from a biological sample obtained from the subject. The biological sample can be a tissue sample or a fluid sample, for example. The biological sample can be a blood sample. Nucleic acids may be fragmented into smaller constituent polynucleotides, prior to analysis.

The potentially pathogenic mutation can include, for example, at least one of (i) a nucleotide sequence mutation encoding an amino acid substitution at an amino acid position selected from the group consisting of M35, S42, E50, V53, D57, Q85, H86, S92, N98, S103, F106, N123, S126, R127, V134, F139, Y150, L152, G176, I182, V203, K254, L264, Q291, V300, A307, F308, G311, P325, P336, G342, D345, A348, I360, I369, P370, H374, I378, R386, and Y388 relative to the wild-type LAL amino acid sequence (SEQ ID NO:2); or (ii) a nucleotide substitution selected from the group consisting of c.1033G>A, c.256C>T, c.309C>A, c.455T>C, c.526G>A, c.538+5G>A, c.931G>A, c.417C>A, c.607G>C, c.253C>A, c.974C>T, c.791T>C, c.294C>G, c.822+1G>C, and c.377C>T relative to the wild-type LIPA nucleotide coding sequence (SEQ ID NO:1). In some embodiments, the mutation is a lysosomal acid lipase (LAL) activity-reducing mutation. Optionally, the mutation occurs in combination with a second mutation in the human LIPA nucleotide sequence, such as a c.894G>A common exon 8 splice junction mutation (E8SJM). The potentially pathogenic mutation may or may not cause a frameshift.

Advantageously, if the detection method yields a positive result, in that one or more of the specified pathogenic LIPA allelic variants is detected in a subject, genetic testing can then be performed on blood relatives in order to determine whether other family members possess the potentially pathogenic LIPA allelic variants.

Detection of a potentially pathogenic LIPA gene variant in a human subject can aid in making, or can confirm, a diagnosis of LAL-D in the subject. Lysosomal storage diseases that can be diagnosed using the diagnostic method of the invention include LAL-D. The nucleotide sequence of LIPA gene of the subject, or associated mRNA or cDNA, is analyzed as in the detection method in order to determine the presence of a mutation associated with reduced LAL activity, wherein reduced LAL activity of the gene variant is consistent with or indicative of LAL-D, and or a clinically identified mutation in the nucleotide sequence of a LIPA gene as described herein. Optionally, the diagnostic method includes determining whether other signs or symptoms associated with LAL-D are present in the subject. This determination can be made before or after genetic analysis to determine whether the subject carries a potentially pathogenic LIPA gene variant. The diagnostic method of the invention, involving the detection of genetic mutations, can also optionally be performed in combination with or as an adjunct to, either before or after, one or more assays for deficient LAL enzyme activity in, for example, dried blood spots. Thus, the diagnostic method of the invention optionally further includes measuring LAL activity in the subject. The level of LAL activity in a patient prior to treatment can be about 1%, about 2%, about 3%, about 5%, about 10%, about 15%, about 20%, about 30%, about 40%, about 50%, about 60%, about 70%, or about 80% of normal levels of LAL activity. For example, the level of LAL activity in a patient prior to treatment can be about 50% or less of normal levels of LAL activity, or about 40% or less of normal levels of LAL activity, or about 30% or less of normal levels of LAL activity, or about 20% or less of normal levels of LAL activity, or about 10% or less of normal levels of LAL activity, or about 5% or less of normal levels of LAL activity. Some patients show no measurable LAL activity prior to treatment. The level of LAL activity in a patient can be measured in cultured cells obtained from a human patient suffering from LAL deficiency.

The diagnostic method can be performed on a subject suspected of having LAL-D, or as a component of a more general genetic screen. For example, a subject can be screened for the presence of a potentially pathogenic LIPA allelic variant in combination with screening for pathogenic gene variants associated with other Mendelian disorders such as phenylketonuria, cystic fibrosis, sickle-cell anemia, oculocutaneous albinism, Huntington's disease, myotonic dystrophy, hypercholesterolemia, neurofibromatosis, polycystic kidney disease, hemophilia, Duchenne's muscular dystrophy, Rett's syndrome, or other Mendelian diseases (see the National Center for Biotechnology Information (NCBI) databases Online Mendelian Inheritance in Man, http://www.ncbi.nlm.nih.gov/omim, and ClinVar, http://www.ncbi.nlm.nih.gov/omim; see also Chial et al., Nature Education 1(1):192 (2008)). The method includes determining the nucleotide sequence of one or more of the patient's LIPA alleles; and determining whether one or more of the patient's LIPA alleles includes a potentially pathogenic mutation as described herein.

In another aspect, the invention provides a kit for detecting a potentially pathogenic mutation in a human LIPA nucleotide sequence. In one embodiment, the kit includes at least one oligonucleotide primer specific for a potentially pathogenic mutation as described herein, and optionallyy, instructions relating to detecting mutations in the LIPA nucleotide sequence. In another embodiment, the kit includes at least one allele-specific oligonucleotide probe for a potentially pathogenic mutation as described herein, and instructions relating to detecting mutations in the LIPA nucleotide sequence.

In another aspect, the invention provides an isolated polynucleotide that includes a mutated human LIPA nucleotide sequence having a nucleotide substitution selected from the group consisting of c.1033G>A, c.256C>T, c.309C>A, c.455T>C, c.526G>A, c.538+5G>A, c.931G>A, c.417C>A, c.607G>C, c.253C>A, c.974C>T, c.791T>C, c.294C>G, c.822+1G>C, and c.377C>T relative to the wild-type LIPA nucleotide coding sequence (SEQ ID NO:1), as well as a vector operably encoding the polynucleotide, and a host cell that includes the vector. Methods of making and using the polynucleotide, vector and host cell are also encompassed by the invention.

Reduction in LAL Activity

Lysosomal Acid Lipase (LAL) is enzyme that has lipase activity. "Reduced LAL activity" is defined in relation to the lipase activity of wild-type human LAL. Lipase activity of the gene products by LAL variants can be measured in an assay that supplies 4-methylumbelliferyl oleate as a substrate, and detects the production of the cleaved fluorophore 4-methylumbelliferyl at excitation/emission wavelengths of 360/460+/−40 nm. Two representative activity assays described in Example II. In the cell lysate assay described in Example II, a LIPA gene product is considered as having "reduced LAL activity" if it exhibits less than 8.5% of wild-type LAL activity. In an assay of cell culture supernatant described in Example II, a LIPA gene product is considered as having "reduced LAL activity" if it exhibits less than 1.5% of wild-type LAL activity. Allelic variants that exhibited reduced LAL activity by either of these two measures are characterized herein as possessing "LAL activity-reducing" mutations. In Example II, over 150 variants, including wild-type LAL, were assayed for LAL activity: 2 variants, including wild-type LAL, known to be non-pathogenic; over 50 variants known to be pathogenic; and over 90 unknown variants. Of the unknown variants, about 29 were shown to have activities low enough, according to one or both activity assays, to suspect pathogenicity, as indicated by the term "suspicious" in the columns labeled "Prediction". Results of the activity assays for the LIPA variants are shown in Table 4. The cutoffs used to determine reduced LAL activity (8.5% for the cell lysate activity, 1.5% for the supernatant activity) can be adjusted. For example, a cutoff value of 1.6%, 1.7%, 1.8%, 1.9%, 2.0%, 2.5%, 3.0%, 3.5%, 4.0%, 4.5%, 5.0%, 5.5%, 6.0% or higher, or any value in between, for the supernatant activity can be used to identify allelic variants having "reduced LAL activity." Likewise, a cutoff value of 9.0%, 9.5%, 10.0%, 10.5%, 11.0%, 11.5%, 12%, 12.5%, 13%, 14%, 15%, 16%, 17%, 18%, 19%, 20% or higher, or any value in between, for the cell lysate activity can be used to identify allelic variants having "reduced LAL activity." The characteristic of "reduced LAL activity" is used to identify mutant LIPA gene products that may be considered potentially pathogenic LIPA variants and thereby indicative of or associated with LAL-D. It should be understood that while the newly identified potentially pathogenic LIPA variants identified herein (i.e., those possessing "LAL activity-reducing mutations) are defined relative to the cutoff values of 8.5% of WT activity for the cell lysate assay or 1.5% for the supernatant assay, additional potentially pathogenic LIPA variants can be identified from Table 4 if the cutoff values are increased.

It should be understood that LIPA gene products exhibiting "reduced LAL activity" include those gene products having no detectable LAL activity. Gene products having no detectable LAL activity may have activity at too low a level to be detected, or they may have no activity at all (i.e., activity has been eliminated).

LAL Activity-Reducing Mutations

FIG. 1 shows a nucleotide sequence of the coding region of the wild-type (normal) human LIPA gene (SEQ ID NO:1) and the amino acid sequence of wild-type (normal) human LAL (SEQ ID NO:2). The newly identified LAL activity-reducing mutations are described with reference to the human LAL wild-type (normal) sequence. It should be understood that one or more of the LAL activity-reducing mutations described herein may occur alone, together, and/or in combination with one or more known mutations in the human LIPA gene.

LAL activity-reducing mutations in a LIPA gene may result in amino acid substitutions at one or more of the amino acid positions in the encoded LAL gene product as shown in Table 1A and/or in Table 4 and/or in the following list of constituent amino acids: M35, S42, E50, V53, D57, S92, F106, N123, S126, R127, V134, Y150, I182, K254, Q291, V300, A307, F308, P336, G342, A348, I360, I369, P370, H374, I378, R386, and Y388, as numbered for human wild-type LAL in FIG. 1.

Potentially pathogenic gene variants may therefore include single base, site specific, or other types of nucleotide sequence mutations that result in amino acid substitutions at one or more of positions M35, S42, E50, V53, D57, S92, F106, N123, S126, R127, V134, Y150, I182, K254, Q291, V300, A307, F308, P336, G342, A348, I360, I369, P370, H374, I378, R386, Y388 and/or positions shown in Table 1A and/or Table 4. Exemplary nucleotide mutations associated with each of these amino acid positions are shown in Table 4.

Exemplary amino acid substitutions yielding a mutant LAL having reduced activity are shown in Table 1A and/or Table 4 and/or include the following: M35T/I, E50G, V53G, D57G, S92C, F106I, N123D, S126F, R127W, Y150C, I182T, K254M, Q291E, A307D, F308V, P336L, G342V, A348V, I360N/T, I369T, H374Y, I378T, R386S, and Y388C. When screening a subject's DNA or RNA for possible pathogenic LIPA allelic variants according to the method of the invention, one of skill in the art can readily determine by inspecting SEQ ID NO:1 (the LIPA nucleotide coding sequence for LAL) which nucleotide base changes relative to the wild-type nucleotide sequence will yield amino acid substitutions. Nucleotide changes that will generate an amino acid substitution at a particular position can be determined with reference to the codon encoding the amino acid at that position in the normal LAL sequence, and there are only a limited number of possibilities permitted by the genetic code.

Exemplary LAL activity-reducing mutations may include mutations that affect precursor mRNA splicing, and/or that include frame shift mutations, such as V134Ffs*4, V300Nfs*30, S42Lfs*6, and P370Rfs*25 and/or as shown in Table 1A and/or Table 4. Exemplary nucleotide mutations associated with each of these amino acid positions are shown in Table 4.

TABLE 1A

Potentially pathogenic LIPA variants

| Amino Acid Position* | Exemplary Amino Acid Mutation |
|---|---|
| M35 | M35T/I |
| S42 | S42Lfs*6 |
| E50 | E50G |
| V53 | V53G |
| D57 | D57G |
| S92 | S92C |
| F106 | F106I |
| N123 | N123D |
| S126 | S126F |
| R127 | R127W |
| V134 | V134Ffs*4 |
| Y150 | Y150C |
| I182 | I182T |
| K254 | K254M |
| Q291 | Q291E |
| V300 | V300Nfs*30 |
| A307 | A307D |
| F308 | F308V |
| P336 | P336L |
| G342 | G342V |
| A348 | A348V |
| I360 | I360N/T |
| I369 | I369T |
| P370 | P370Rfs*25 |
| H374 | H374Y |
| I378 | I378T |
| R386 | R386S |
| Y388 | Y388C |

*Position as specified in wild-type human LAL (SEQ ID NO: 2)

The newly identified LAL activity-reducing mutations identified herein can occur alone or in combination with each other or with one or more known pathogenic mutations in the nucleotide sequence of the human LIPA gene. Exemplary known amino acid substitutions resulting in pathogenic allelic variants (including those that are newly identified in Example I) are shown in Table 4 and/or include the following: Y43X, D57V, R65X, Q85K, Q85R, H86Y, G87V, W95R, N98K, S103R, W116X, N119S, R121G, S126F, H129R, H129P, S133X, F139L, W140X, D145E, L152P, G176S, L200P, P202L, V203L, R218X, P220S, L264P, G266X, N271H, T288I, S289C, L294S, H295Y, Q298H, Q298X, G311R, Y324X, P325L, G342R, G342W, D345N and L357P, where "X" indicates a stop codon. Exemplary known frame shift mutations resulting in pathogenic allelic variants are shown in Table 4 and/or include the following: P212Lfs*5, F228Lfs*13, S323Lfs*44, T327Nfs*4, G343Vfs*15, W242Gfs*12, N161Ifs*19, A199Cfs*13, F139Ifs*7, and I107Hfs*4.

Clinically Identified LIPA Mutations

This disclosure also describes novel clinically identified mutations in the nucleotide sequence of a human LIPA gene. These mutations are likewise of clinical and research interest because they were discovered in patients who have been diagnosed with LAL-D. It is expected that the identification of these additional mutations in the nucleotide sequence of a human LIPA gene will be of important medical significance in that it will improve genetic screening for human subjects suspected of having LAL-D.

As noted earlier, the mutation in the nucleotide sequence of the human LIPA gene can, in some embodiments, result in an amino acid substitution in the LAL encoded by the mutated LIPA gene. In some embodiments, the mutation causes a truncation of LAL. The mutation can be, for example, a missense mutation or a nonsense mutation. In some embodiments, the mutation causes misregulation of precursor RNA splicing, and/or alternative precursor mRNA splicing. In some embodiments, the mutation can include an insertion or deletion and may cause a frameshift in the LAL encoded by the mutated LIPA gene. A mutation can occur in an exon or an intron; a mutation in an intron may not alter the LAL coding sequence, but may, for example, affect splicing.

Thirteen additional potentially pathogenic mutations were discovered through analysis of the LIPA gene of 66 LAL-D patients participating in a clinical trial (the ARISE study) for sebelipase alfa (see Example I). Seven novel LIPA mutations, namely, c.1033G>A, c.256C>T, c.309C>A, c.455T>C, c.526G>A, c.538+5G>A, and c.931G>A, where "c." designates numbering according to the coding sequence, were found to be present in combination with the known pathogenic mutation c.894G>A. Six novel LIPA mutations, namely, c.417C>A, c.607G>C, c.253C>A, c.974C>T, c.791T>C, and c.294C>G, were found to be present in combination with pathogenic non-E8SJM LIPA mutations. The numbering system for the LIPA gene coding region is shown in FIG. 1.

Two additional potentially pathogenic mutations, c.822+1G>C and c.377C>T, were discovered through analysis of the LIPA gene of 31 LAL-D participating in another clinical trial (the CLOG study) for sebelipase alfa (Example I).

These mutations in the nucleotide sequence of the LIPA gene may result in amino acid substitutions at one or more of the amino acid positions in the encoded LAL gene product as shown in Table 1B and/or in Table 4 and/or in the following list of constituent amino acids: Q35, H86, N98, S103, S126, F139, L152, G176, V203, L264, G311, P325, and D345, as numbered for human wild-type LAL in FIG. 1.

Potentially pathogenic gene variants may therefore include single base, site specific, or other types of nucleotide sequence mutations that result in amino acid substitutions at one or more of positions Q35, H86, N98, S103, S126, F139, L152, G176, V203, L264, G311, P325, and D345 and/or positions shown in Table 1B and/or in Table 4.

Exemplary amino acid substitutions are shown in Table 1B and/or in Table 4 and/or include the following: Q85K, H86Y, N98K, S103R, S126F, F139L, L152P, G176S, V203L, L264P, G311R, P325L, and D345N. When screening a subject's DNA or RNA for possible pathogenic LIPA allelic variants according to the method of the invention, one of skill in the art can readily determine by inspecting SEQ ID NO:1 (the LIPA nucleotide coding sequence for LAL) which additional nucleotide base substitutions, if any, will yield in the indicated substitutions based on the codon encoding the starting amino acid, as there are only a limited number of possibilities permitted by the genetic code.

TABLE 1B

Clinically identified pathogenic mutations

| Mutation | Amino Acid Position* | Exemplary Amino Acid Mutation |
|---|---|---|
| c.253C > A | Q85 | Q85K |
| c.256C > T | H86 | H86Y |
| c.294C > G | N98 | N98K |
| c.309C > A | S103 | S103R |
| c.377C > T | S126 | S126F |
| c.417C > A | F139 | F139L |
| c.455T > C | L152 | L152P |
| c.526G > A | G176 | G176S |
| c.538 + 5G > A | N/A | N/A |
| c.607G > C | V203 | V203L |
| c.791T > C | L264 | L264P |

TABLE 1B-continued

Clinically identified pathogenic mutations

| Mutation | Amino Acid Position* | Exemplary Amino Acid Mutation |
|---|---|---|
| c.822 + 1G > C | N/A | N/A |
| c.931G > A | G311 | G311R |
| c.974C > T | P325 | P325L |
| c.1033G > A | D345 | D345N |

*Position as specified in wild-type human LAL (SEQ ID NO: 2)

LIPA Gene Variant Detection

The invention includes a method for detecting the presence or absence of an LAL activity-reducing mutation or a novel clinically identified mutation in the nucleotide sequence of a LIPA gene of a human subject. Any one or more of the LAL activity-reducing mutations or the novel clinically identified mutations described herein can be detected. The presence of one or more LIPA alleles possessing an LAL activity-reducing mutation or clinically identified mutation as described herein (i.e., one or more potentially pathogenic LIPA gene variants) has clinical relevance to the diagnosis of LAL-D.

Detection of a mutation in the nucleotide sequence of a LIPA gene can be accomplished using any convenient method. Many techniques for genetic testing and genetic analysis are known to the art. Genetic analysis for the presence of a potentially pathogenic LIPA gene variant in a subject can be carried out, for example, using recently developed nucleotide sequencing technologies or using traditional hybridization technologies. For example, the analysis can be carried out using positional cloning based on linkage analysis and/or Sanger sequencing. Another option is RNA whole transcriptome sequencing, which may also be referred to as RNA sequencing, RNA-seq or whole transcriptome shotgun sequencing (WTSS), which typically utilizes next-generation sequencing technologies (NGS) and focuses on a gene expression profile, is able to detect alternative splicing events, and can detect single nucleotide variants. Another option is exome sequencing or whole exome sequencing (WES or WXS), wherein some or all of the expressed genes in a genome (i.e., the exome) are sequenced. Whole-exome sequencing facilitates identification of autosomal recessive disease genes in single patients from non-consanguineous families. Another option is whole-genome sequencing (WGS) which provides a complete view of the human genome, including point mutations in distant enhancers and other regulatory elements. Pabinger et al., Brief. Bioinform (2014) 15(2):256-278, Epub Jan. 21, 2013. Other exemplary methods of genetic analysis include, but are not limited to, restriction fragment length polymorphism identification (RFLPI) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads. It should be understood that mutation analysis and detection techniques are rapidly evolving and detection of a potentially pathogenic LIPA gene variant is not limited to any particular detection technique.

Mutations in the nucleotide sequence of a LIPA gene can be detected by analyzing any polynucleotide or polynucleotide fragment that derives from, directly or indirectly the LIPA gene of a subject. Types of polynucleotides that can be analyzed for mutations include, without limitation, genomic DNA (whole or partial), exomic RNA (whole or partial), primary RNA transcripts such as precursor RNA, processed RNA such as spliced mRNA, mature RNA and mRNA, and cDNA. The nucleotide sequence to be analyzed typically includes coding sequences, for example exon sequences, and may also include intron sequences, particularly intron sequences that proximal to splice junctions and may thus affect production of the mature mRNA and/or protein translation and structure.

The nucleic acids (e.g., DNA or RNA) to be analyzed for presence of one or more LAL activity-reducing LIPA and/or novel clinically identified gene mutations can be present in or isolated from a biological sample obtained from the subject. The biological sample can be a tissue sample or a fluid sample, for example. The subject can be a child or an adult. Nucleic acids may be fragmented into smaller constituent polynucleotides, prior to analysis.

Advantageously, if the detection method yields a positive result, in that one or more of the specified pathogenic LIPA allelic variants is detected in a subject, genetic testing can then be performed on blood relatives in order to determine whether other family members possess the potentially pathogenic LIPA allelic variants.

Activity Assay Using Natural Substrate

Unexpectedly, some LIPA variants that are known to be pathogenic were nonetheless shown to have significant activity in a LAL activity assay that utilizes the artificial substrate 4-MU oleate (see Table 4). As a result, some potentially pathogenic LIPA variants may escape detection if the only activity assay used to screen for them is a LAL activity assay utilizing 4-MU oleate. The invention thus encompasses the use of other substrates, particularly natural substrates, in a LAL activity assay to detect potentially pathogenic LIPA variants. In one embodiment, the invention contemplates the use of a LAL activity assay that utilizes a natural, physiological substrate, such as a cholesteryl ester or a triglyceride, to identify as potentially pathogenic those LIPA variants with significantly reduced activity toward the natural substrate (e.g., below 10% of wild-type level), particularly those LIPA variants that may show relatively normal activity in a LAL activity assay utilizing the artificial substrate 4-MU oleate. A human LIPA nucleotide sequence containing at least one mutation can be expressed in a host cell, the expressed LAL can be contacted with a natural substrate, such as a triglyceride, for example triacylglycerol, or a cholesteryl ester, for example cholesteryl oleate, and the LAL activity level of the expressed LAL acting on the natural substrate can be quantitated. A LAL activity level that is less than the LAL activity level of a wild-type human LAL using the same substrate is indicative of a potentially pathogenic mutation in the human LIPA nucleotide sequence. In other words, a LAL having reduced LAL activity compared to a wild-type LAL, according to an activity assay that utilizes a natural, physiological substrate, is potentially pathogenic. In some embodiments, a LAL having reduced activity has less than 10% of the activity of a wild-type LAL in an assay that utilizes the natural substrate. The cutoff value can, however, be readily adjusted lower or higher; thus, a cutoff value of 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12%, 12.5%, 13%, 14%, 15%, 16%, 17%, 18%, 19%, 20% or higher, or any value in between, of the activity of a wild-type LAL can be used to identify allelic variants having "reduced LAL activity" in an assay that utilizes a natural LAL substrate.

Some of the LIPA variants that are identified as potentially pathogenic by way of an assay that utilizes a natural substrate may nonetheless show normal or relatively normal activity (e.g., greater than 10%, 20%, 30%, 40%, or 50% of the LAL activity level of the wild-type human LAL) when LAL activity level is measured in an assay utilizing an artificial substrate. Employing a natural substrate in a LAL assay may therefore advantageously allow identification of potentially pathogenic LIPA variants that would not be identified if only LAL activity toward an artificial substrate is evaluated. The method permits evaluation of any known human LIPA nucleotide sequence, such as those variants cataloged in the Exome Aggregation Consortium (ExAC) database, for potential pathogenicity. For example, those LIPA variants that have been classified in Table 4 as "normal" on the basis of a 4-MU oleate activity assay can be re-evaluated for LAL activity utilizing a natural substrate in order to identify additional potentially pathogenic LIPA variants.

Without intending to be bound by theory, it is postulated that mutations in the LIPA gene that yield a LAL exhibiting substantially reduced activity when a natural, physiological substrate is used but which do not significantly affect LAL activity when 4-MU is utilized as a substrate may be located in or near the putative lid domain of the LAL structure (see FIG. 4). The lid domain may be involved in substrate binding; thus, mutations in or near the lid domain may affect substrate specificity. In Example III, it is shown that 4 of the 5 LIPA variants that are known to be pathogenic but that exhibited relatively normal activity in a 4-MU oleate activity assay map to the lid domain, and the fifth mutation is close to the lid domain.

Diagnostic Methods

Detection of a potentially pathogenic LIPA gene variant in a human subject can aid in making, or can confirm, a diagnosis of LAL-D in the subject. Lysosomal storages diseases that can be diagnosed using the diagnostic method of the invention include Wolman Disease and Cholesteryl Ester Storage Disease (CESD). The nucleotide sequence of LIPA gene of the subject, or associated mRNA or cDNA, is analyzed as in the detection method in order to determine the presence of a mutation associated with reduced LAL activity, wherein reduced LAL activity of the gene variant is consistent with or indicative of LAL-D, and or a clinically identified mutation in the nucleotide sequence of a LIPA gene as described herein. Optionally, the diagnostic method includes determining whether other signs or symptoms associated with LAL-D, particularly CESD, are present in the subject. This determination can be made before or after genetic analysis to determine whether the subject carries a potentially pathogenic LIPA gene variant. Signs and symptoms that can be evaluated or detected include, without limitation, hypercholesterolemia, hypertriglyceridemia, HDL deficiency with abnormal lipid deposition in one or more organs, mixed hyperlipidemia with low HDL-cholesterol levels, abnormally enlarged liver (hepatomegaly), hepatic steatosis, fibrosis of the liver, abnormally enlarged spleen (splenomegaly), abnormally enlarged adrenal glands (adrenomegaly), elevated transaminases, and/or, in general, a serum lipid profile that is characterized by high total serum concentrations of cholesterol, low-density lipoprotein, and triglycerides; and low serum concentration of high-density lipoprotein. The diagnostic method of the invention, involving the detection of genetic mutations, can also optionally be performed in combination with or as an adjunct to, either before or after, one or more assays for deficient LAL enzyme activity in peripheral blood leukocytes, fibroblasts, or dried blood spots. Thus, the diagnostic method of the invention optionally further includes measuring LAL activity in the subject. The level of LAL activity in a patient prior to treatment can be about 1%, about 2%, about 3%, about 5%, about 10%, about 15%, about 20%, about 30%, about 40%, about 50%, about 60%, about 70%, or about 80% of normal levels of LAL activity. For example, the level of LAL activity in a patient prior to treatment can be about 50% or less of normal levels of LAL activity, or about 40% or less of normal levels of LAL activity, or about 30% or less of normal levels of LAL activity, or about 20% or less of normal levels of LAL activity, or about 10% or less of normal levels of LAL activity, or about 5% or less of normal levels of LAL activity. Some patients show no measurable LAL activity prior to treatment.

The level of LAL activity in a patient can be measured in cultured fibroblasts or lymphocytes (e.g., leukocytes) obtained from a human patient suffering from LAL deficiency. Lymphocytes include, but are not limited to, peripheral blood mononuclear cells (PMBC). Methods for the measurement are described, for example, in Burton et al., (1980) *Clinica Chimica Acta* 101: 25-32, and in Anderson et al., (1999) *Mol. Genet. & Metab.*, 66: 333-345. LAL deficient patients who are to be treated with exogenous LAL can exhibit fibroblast or leukocyte LAL enzymatic activity that is less than about 30, about 20, about 10, about 5, about 4, about 3, about 2 or about 1 pmol/mg/min as measured using triolein or cholesteryl oleate as a substrate. See U.S. Pat. No. 8,663,631.

The diagnostic method can be performed on a subject suspected of having LAL-D, or as a component of a more general genetic screen. For example, a subject can be screened for the presence of a potentially pathogenic LIPA allelic variant in combination with screening for pathogenic gene variants associated with other Mendelian disorders such as phenylketonuria, cystic fibrosis, sickle-cell anemia, oculocutaneous albinism, Huntington's disease, myotonic dystrophy, hypercholesterolemia, neurofibromatosis, polycystic kidney disease, hemophilia, Duchenne's muscular dystrophy, Rett's syndrome, or other Mendelian diseases (see the National Center for Biotechnology Information (NCBI) databases Online Mendelian Inheritance in Man, http://www.ncbi.nlm.nih.gov/omim, and ClinVar, http://www.ncbi.nlm.nih.gov/omim; see also Chial et al., Nature Education 1(1):192 (2008)).

The diagnostic method of the invention optionally includes treating the patient for LAL-D.

Treatment Methods

The invention also includes treating a patient who has been found to carry a potentially pathogenic LIPA variant as described herein. Such a patient is either afflicted with, or suspected of being afflicted with, LAL-D. In some embodiments, the patient is treated with enzyme replacement therapy, for example by using recombinant LAL. A patient who has been found to carry a potentially pathogenic LIPA variant can be treated by administering a therapeutically effective amount of exogenous lysosomal acid lipase (LAL). The exogenous LAL can be a recombinant human LAL as described, for example, in U.S. Pat. No. 8,663,631 and U.S. Publ. 20130209436, and may have an N-linked glycan structure that includes at least one mannose and/or mannose-6-phosphate. Sebelipase alfa is a suitable enzyme replacement therapy that is approved for the treatment of patients with lysosomal acid lipase deficiency (LAL-D) and is typically administered via intravenous injection or infusion (Burton et al., New Eng. J. Med. 373:1010-1020 (2015)). The exogenous LAL may be effectively internalized into the lysosome of, e.g., lymphocytes, macrophages, and/or fibroblasts, and may cause an increase in LAL activity in the patient. An increase in LAL activity can be measured, for example, in lymphocytes and/or fibroblasts as described herein and in more detail in U.S. Pat. No. 8,663,631.

The method for treating a patient who has been found to carry a potentially pathogenic LIPA variant can include administering a therapeutically effective amount of exogenous LAL protein to the patient one time every 5 days to one time every 30 days. The patient can be dosed about 0.1 mg to about 50 mg of exogenous LAL per kilogram of body weight. For example, the patient can be dosed about 0.1 mg to about 10 mg of exogenous LAL per kilogram of body weight, or about 0.1 mg to about 5 mg of exogenous LAL per kilogram of body weight. The infusion rate can be between about 0.1 mg/kg/hr and about 4 mg/kg/hr. In an exemplary protocol, patients with rapidly progressive LAL-D presenting within the first six months of life can be treated with exogenous LAL at a dosage of 1 mg/kg administered once weekly as an intravenous infusion, which can be increased to 3 mg/kg once weekly to achieve the desired clinical response. In another exemplary protocol, pediatric and adult patients with LAL-D can be treated with exogenous LAL at a dosage of 1 mg/kg administered once every other week as an intravenous infusion. Exemplary administration and dosing protocols, as well as suitable pharmaceutical compositions, are exemplified in U.S. Pat. No. 8,663,631; see also WO/2012/050695 and WO/2011/133960. Other treatment methods include the administration of therapeutic polynucleotides as in US2014/0155475.

Optionally, the patient is treated with a second therapeutic. The second therapeutic can include, for example, a cholesterol-reducing drug (e.g., statin or ezetimibe), an antihistamine (e.g., diphenhydramine), or an immunosuppressant. Nonlimiting examples of antihistamines include antihistamines include, without limitation, clemastine, doxylamine, loratidine, desloratidine, fexofenadine, pheniramine, cetirizine, ebastine, promethazine, chlorpheniramine, levocetirizine, olopatadine, quetiapine, meclizine, dimenhydrinate, embramine, dimethidene, and dexchloropheniramine. Nonlimiting examples of immunosuppressants include antihistamines, corticosteroids, sirolimus, voclosporin, ciclosporin, methotrexate, IL-2 receptor directed antibodies, T-cell receptor directed antibodies, TNF-alpha directed antibodies or fusion proteins (e.g., infliximab, etanercept, or adalimumab), CTLA-4-Ig (e.g., abatacept) and anti-OX-40 antibodies. Nonlimiting examples of cholesterol-reducing drugs include examples of such agents include: atorvastatin (Lipitor® and Torvast®), fluvastatin (Lescol®), lovastatin (Mevacor®, Altocor®, Altoprev®), pitavastatin (Livalo®, Pitava®), pravastatin (Pravachol®, Selektine®, Lipostat®), rosuvastatin (Crestor®), and simvastatin (Zocor®, Lipex®).

Expression of Variant LIPA Nucleotide Sequences

As will be appreciated by a person of skill in the art, a nucleotide sequence encoding an LAL can be introduced into and optionally expressed in a host cell, and the invention encompasses methods for introducing LAL-encoding nucleotide sequences into host cells and optionally expressing them. Introducing a potentially pathogenic LIPA gene variant nucleotide sequence into a host cell and optionally expressing a LAL encoded by the variant can be achieved through any of a number of molecular biology techniques. Typically, the polynucleotide encoding the LAL is introduced into the cell using a vector. The vector can be a cloning vector, a shuttle vector, or an expression vector, depending on the intended purpose. The polynucleotide may be circular or linear, single-stranded or double stranded, and can be DNA, RNA, or any modification or combination thereof. The vector can be any molecule that may be used as a vehicle to transfer genetic material into a host cell. Examples of vectors include plasmids, viral vectors, cosmids, and artificial chromosomes, without limitation. Examples of molecular biology techniques used to transfer nucleotide sequences into a microorganism include, without limitation, transfection, electroporation, infection, transduction, and transformation. These methods are routine and known in the art. Insertion of a vector into a target cell is usually called transformation for bacterial cells and transfection for eukaryotic cells, however insertion of a viral vector is often called transduction. The terms transformation, transfection, infection, and transduction, for the purpose of the present invention, are used interchangeably herein.

An "expression vector" or "expression construct" is any vector that is used to introduce a specific polynucleotide into a target cell such that once the expression vector is inside the cell, the protein that is encoded by the polynucleotide is produced by the cellular transcription and translation machinery. The expressed protein is referred to herein as "operably encoded" by the expression vector. Typically, an expression vector includes regulatory sequences operably linked to the polynucleotide encoding the desired enzyme. Regulatory sequences are common to the person of the skill in the art and may include for example, an origin of replication, a promoter sequence, and/or an enhancer sequence. An expression vector may include a ribosome binding site (RBS) and a start site (e.g., the codon ATG) to initiate translation of the transcribed message to produce the polypeptide. A vector may also include a termination sequence to end translation.

The polynucleotide encoding the desired enzyme can exist extrachromosomally or can be integrated into the host cell chromosomal DNA. Typically, extrachromosomal DNA is maintained within the vector on which it was introduced into the host cell. In many instances, it may be beneficial to select a high copy number vector in order to maximize the expression of the enzyme. The host cell can be a prokaryotic or eukaryotic host cell. An exemplary host cell is Expi293F as described in Example II. Alternative methods of cloning, amplification, expression, and purification will be apparent to the skilled artisan. Representative methods are disclosed in Sambrook, Fritsch, and Maniatis, Molecular Cloning, a Laboratory Manual, 2nd Ed., Cold Spring Harbor Laboratory (1989).

The method of the invention further includes expressing the gene product from an uncharacterized LIPA gene variant in a host cell, and evaluating LAL expression levels in order to determine whether the LIPA gene variant is potentially pathogenic, as exemplified in the Examples.

Kits

Also provided is a kit for detecting an LAL activity-reducing mutation or a novel clinically identified mutation in the nucleotide sequence of a human LIPA gene. In one embodiment, the kit includes at least one oligonucleotide primer specific for an LAL activity-reducing LIPA gene mutation or clinically identified mutation as described herein. In another embodiment, the kit includes at least one allele-specific oligonucleotide probe for an LAL activity-reducing LIPA gene mutation or a clinically identified mutation as described herein. Optionally, the kit includes instructions relating to detecting mutations in the LIPA gene.

Advantageously, the kit can contain primers or probes of sufficient number and variety so as to screen for a multiplicity of mutations in the nucleotide sequence of the human LIPA gene, thereby increasing the diagnostic power of the kit. The kit may contain probes and/or primers that are capable of detecting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more mutations in the nucleotide sequence of a human LIPA gene.

EXAMPLES

The invention is illustrated by the following examples. It is to be understood that the particular examples, materials, amounts, and procedures are to be interpreted broadly in accordance with the scope and spirit of the invention as set forth herein.

Example I

Novel LIPA Mutations Associated With Lysosomal Acid Lipase Deficiency

Lysosomal Acid Lipase Deficiency (LAL-D) is a life-threatening genetic disease caused by mutations in the lysosomal acid lipase (LIPA) gene with a clinical spectrum from infancy to adulthood, similar to other lysosomal storage disorders. Disease awareness is low and the number of known pathogenic mutations is small. Additional analysis is needed to better understand the underlying genetic architecture of the lysosomal acid lipase (LIPA) enzyme and associated diminished activity introduced by the combined genetic mutations on each LIPA allele.

Methods: Participants in both the ARISE study (NCT 01757184; see https://clinicaltrials.gov/ct2/show/NCT01757184/, a phase 3, multi-center, randomized, placebo-controlled study of sebelipase alfa, 66 patients, which included 47 children (>4 to <18 years of age) and 19 adults (≥18 years of age) with LAL-D), and the CLOG study (NCT02112994; see https://clinicaltrials.gov/ct2/show/NCT02112994/, a multicenter, open-label, single-arm study of sebelipase alfa in 31 children (>8 months of age) and adults with LAL-D) had genetic analysis of the LIPA gene, in addition to undergoing dried blood spot testing to demonstrate reduced LAL enzyme activity consistent with LAL-D (Hamilton et al., P. Clin Chim Acta. 2012; 413(15-16):1207-1210). Isolation of DNA and genetic mutation analysis for allelic variants of the LIPA gene was performed (Prevention Genetics, Marshfield, Wis., US).

Results: Overall, 85% (56/66) of subjects from the ARISE study had at least one copy of the previously described c.894G>A common exon 8 splice junction mutation (E8SJM) (Aslanidis et al., Genomics 1996; 33:85-93; Klima et al., J Clin Invest 1993; 92:2713-2718), 32% homozygotes (21/66) and 53% compound heterozygotes (35/66), resulting in an E8SJM allele frequency of 58% (77/132) in this study. Seven novel LIPA mutations paired with c.894G>A were discovered (c.1033G>A, c.256C>T, c.309C>A, c.455T>C, c.526G>A, c.538+5G>A, and c.931G>A) and six novel LIPA mutations were discovered in combination with pathogenic non-E8SJM LIPA mutations (c.417C>A, c.607G>C, c.253C>A, c.974C>T, c.791T>C, and c.294C>G). These 13 novel pathogenic LIPA mutations identified from the ARISE study are shown in Table 2, with at least 1 patient being compound heterozygous for novel mutations. Each of these novel mutations was a missense mutation in a protein coding region with the exception of c.538+5G>A, an intronic, single nucleotide polymorphism (SNP), which is likely impacting exon splicing. A subset of 8 novel mutations, shown in bold, was analyzed in silico. These variants were flagged as being deleterious by a consensus score of four standard in silico prediction tools: MutationTaster, PolyPhen2, SIFT, and Provean—the only exception was c.791T>C, which was flagged as benign by PolyPhen2. Each of these 8 novel missense mutations are located close to a previously reported pathogenic mutation and are either close to one of the three LIPA catalytic triad locations (S174, D345, and H374), or close to the lid region which binds the LIPA substrate, as shown in FIG. 5.

TABLE 2

LIPA Genotypes With Novel Mutations Identified in Patients With LAL-D From the ARISE Study

| Allele 1 | Allele 2 |
| --- | --- |
| c.894G > A | c.1033G > A |
| c.894G > A | c.256C > T |
| c.894G > A | c.309C > A |
| c.894G > A | c.455T > C |
| c.894G > A | c.526G > A |
| c.894G > A | c.538 + 5G > A |
| c.894G > A | c.931G > A |
| c.193C > T | c.417C > A |
| c.153C > A | c.607G > C |
| c.607G > C | c.791T > C |
| c.386A > G | c.253C > A |
| c.253C > A | c.294C > G |
| c.676 − 2A > G | c.974C > T |

Two additional novel pathogenic LIPA mutations, c.822+1G>C and c.377C>T, were discovered in study CL06.

Selected novel LIPA missense mutations identified in patients from the ARISE and CL06 studies are summarized in Table 3.

TABLE 3

Selected Novel LIPA Missense Mutations Identified in Patients From the ARISE and CL06 Studies

| cDNA Representation | Protein Rep. | Nearest Known[a] | Known Distance[b] | Nearest Triad[c] | Triad Distance[d] | Lid Domain[e] |
| --- | --- | --- | --- | --- | --- | --- |
| c.256C > T | H86Y | Q85R, G87V | 1 | S174 | 88 | no |
| c.309C > A | S103R | W95R | 8 | S174 | 71 | no |
| c.417C > A | F139L | D145E | 6 | S174 | 35 | no |
| c.526G > A | G176S | L200P | 24 | S174 | 2 | no |
| c.791T > C | L264P | N271H | 7 | D345 | 81 | yes |
| c.931G > A | G311R | Q298H | 13 | D345 | 34 | yes |
| c.974C > T | P325L | G342R | 17 | D345 | 20 | no |
| c.377C > T | S126F | N129R | 3 | S174 | 48 | no |

[a]The nearest location of a previously reported pathogenic LIPA mutation (see, Reiner Z, Guardamagna O, Nair D, et al. Atherosclerosis. 2014; 235(1): 21-30).
[b]Distance of the novel mutation from the nearest location of a previously reported pathogenic mutation along the LIPA amino acid sequence.
[c]Location of the nearest LIPA catalytic triad, one of three amino acids critical to the protein's enzymatic activity.
[d]Distance of the novel mutation from the nearest location of a catalytic triad.
[e]The mutation in the lid region of the enzyme, inhibiting ability to bind to substrate.

Figure 6:
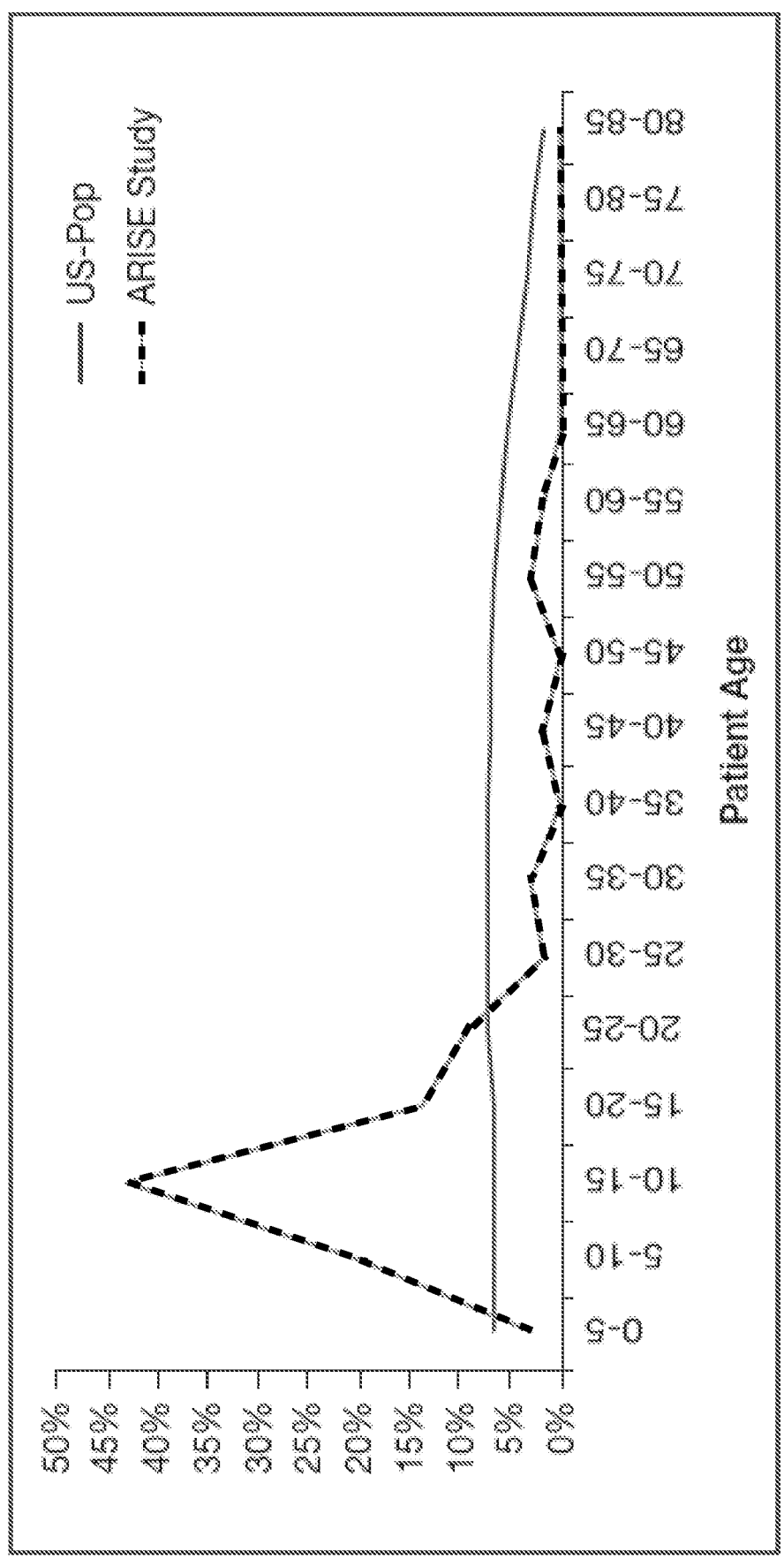
FIG. 6 shows the age distribution of patients, as a percentage of the total, in the ARISE study (NCT 01757184; see https://clinicaltrials.gov/ct2/show/NCT01757184/) compared to the general population.

Discussion: The 13 novel mutations from the ARISE study, together with two additional mutations discovered in the CL06 study, have been identified in diagnosed patients with LAL-D and represent a substantial increase over the ~60 published pathogenic LIPA mutations which will assist in accurate diagnosis. Missense mutations were found to lie near previously reported pathogenic mutations, within the catalytic domain, or within the substrate-binding domain of LIPA The E8SJM variant, which is a well-established prevalent mutation in LAL-D patients, was found with 58% allelic frequency in the patients in the ARISE study; this is consistent with data from an earlier assessment of 135 patient cases with LAL-D, wherein the E8SJM variant represented 61% of the overall allele count (see, Bernstein D L, Hulkova H, Bialer M G, Desnick R J. J Hepatol. 2013; 58(6):1230-1243). The age distribution of patients in the ARISE study was found to be heavily skewed towards a young population (FIG. 6), which is consistent with the analysis of Burton et al. (Burton B K, Deegan P B, Enns G M, et al. J Pediatr Gastroenterol Nutr. 2015; 61(6):619-625), which revealed that 18.7% of LAL-D patients were ≥40 years of age as compared with 46.7% in a representative population. The observation of a young population identified with LAL-D could be due to an under-representation of older subjects carrying the E8SJM variant, as they are more likely to never be diagnosed or to be diagnosed later in life after the disease advances or they may not survive to adulthood.

Example II

Functional Characterization of Novel LIPA Variants Found Within the ExAC Database to Estimate the Overall Prevalence of Lysosomal Acid Lipase Deficiency Lysosomal acid lipase deficiency (LAL-D) is a rare metabolic disease characterized by the accumulation of cholesteryl esters and triglycerides within lysosomes. The prevalence of LAL-D has been estimated at 1 in 130,000 within Caucasian and Hispanic populations. This is based on the assumption that 60% of these patients harbor the c.894G>A LIPA mutation (the gene that encodes LAL) (Scott et al., Hepatology, 2013, 58(3), 958-65; Epub 2013 Jul. 29). However, the prevalence of LAL-D outside of these population groups is not well defined given that c.894G>A mutation is rarely found in non-Caucasian and non-Hispanic LAL-D patients. LAL-D is cataloged in the Online Mendelian Inheritance in Man (OMIM) database as number 278000 (Online Mendelian Inheritance in Man database. Lysosomal acid lipase deficiency (#278000) (http://omim.org/entry/278000)).

Due to the rapid growth of whole exome sequencing, there are now large, publically available datasets of gene variants with their corresponding allele frequency across different ethnic groups. In theory, these datasets could be used to predict the prevalence of a particular genetic disease. However this approach is limited in that a large number of variants are of unknown significance and their contribution to disease is unclear. For example, there over 100 LIPA missense variants found in the Exosome Aggregation Consortium (ExAC) database, which are derived from ~60,000 individual genomes. Of these variants, at least 30 are characterized as disease associated and two are normal, non-pathogenic variants (the wild-type LAL as defined here, and a variant that has been described in the NCBI ClinVar database as NM_000235.3(LIPA):c.46A>C (p.Thr16Pro). The remaining LIPA missense variants are uncharacterized and cannot be used in estimates of LAL-D prevalence.

To overcome this issue, we expressed LIPA missense variants in Expi293 cells then determined LAL activity using the artificial substrate 4-methylumbelliferyl oleate. Most confirmed pathogenic mutations display less than 8.5% intracellular activity in the LAL activity assay and/or less than 1.5% activity in supernatants. Table 4 shows activity data and specifies 8.5% intracellular LAL activity or 1.5% LAL activity in supernatants as a cut-off value to define a disease-causing variant; however, this cut-off value is not immutable, and variants displaying higher activity levels may also be disease-causing. It will be noted that there are some outliers where mutations that potentially pathogenic based on being found in a LAL-D patient nonetheless show relatively normal lipase activity (e.g. variant V203L); thus, there may be other mechanisms at play beyond simply lipase activity that can result in disease.

Using 8.5% intracellular LAL activity or 1.5% LAL activity in supernatants as a cut-off value, we discovered a large number of uncharacterized LIPA variants that are likely pathogenic. The results of this analysis suggest that a greater number of mutations contribute to the incidence of LAL-D than current estimates, and also highlights the value in combining population-wide gene variant data with in vitro enzyme activity assays to build prevalence estimates for metabolic diseases.

TABLE 4

| Variant (Protein) | Residue | Variant (nucleic acid) | Plasmid ID | Pathogenic* | Western Blot Intracellular | Western Blot Secreted | Lipase Activity (% WT) Intracellular Mean | Lipase Activity (% WT) Intracellular SD | Lipase Activity (% WT) Supernatant Mean | Lipase Activity (% WT) Supernatant SD | Prediction** <8.5% intracellular activity | Prediction** <1.5% activity in supernatant | Prediction** Overall (<8.5% or <1.5% or both) |
|---|---|---|---|---|---|---|---|---|---|---|---|---|---|
| G7E | 7 | 20 G > A | LAL170 | Unknown | Yes | Yes | 60.78 | 23.15 | 73.23 | 35.52 | Normal | Normal | Normal |
| V10I | 10 | 28 G > A | LAL176 | Unknown | Yes | Yes | 69.53 | 27.18 | 74.65 | 37.06 | Normal | Normal | Normal |
| V13I | 13 | 37 G > A | LAL179 | Unknown | Yes | Yes | 50.83 | 25.54 | 45.24 | 19.55 | Normal | Normal | Normal |
| T16P | 16 | 46 A > C | LAL061 | No | Yes | Yes | 139.06 | 73.07 | 127.81 | 75.51 | N/A | N/A | N/A |
| G23R | 23 | 67 G > A | LAL062 | Unknown | Yes | Yes | 112.75 | 61.46 | 107.45 | 54.67 | Normal | Normal | Normal |
| P31R | 31 | 92 C > G | LAL106 | Unknown | Yes | Yes | 51.25 | 17.41 | 7.25 | 0.55 | Normal | Normal | Normal |
| P31R | 31 | 92 C > G | LAL209 | Unknown | Yes | Yes | 51.57 | 10.09 | 9.41 | 2.80 | Normal | Normal | Normal |
| M35T | 35 | 104 T > C | LAL107 | Unknown | Yes | Low | 27.55 | 10.27 | 0.90 | 0.22 | Normal | Suspicious | Suspicious |
| M35T | 35 | 104 T > C | LAL156 | Unknown | Yes | Low | 25.72 | 6.74 | 1.05 | 0.48 | Normal | Suspicious | Suspicious |
| M35I | 35 | 105 G > A | LAL157 | Unknown | Yes | Low | 20.75 | 8.47 | 1.13 | 0.25 | Normal | Suspicious | Suspicious |
| S42F | 42 | 125 C > T | LAL165 | Unknown | Yes | Yes | 43.60 | 17.00 | 14.17 | 7.34 | Normal | Normal | Normal |
| S42Lfs*6 | 42 | 125 del CT | LAL146 | Unknown | Low | No | 0.63 | 0.57 | 0.14 | 0.19 | Suspicious | Suspicious | Suspicious |
| Y43X | 43 | 129 C > G | LAL086 | Yes | Low | No | 0.13 | 0.62 | 0.26 | 0.21 | N/A | N/A | N/A |
| W44G | 44 | 130 T > G | LAL166 | Unknown | Yes | Low | 27.69 | 10.12 | 2.20 | 0.51 | Normal | Normal | Normal |
| P47H | 47 | 140 C > A | LAL108 | Unknown | Yes | Yes | 65.43 | 14.29 | 8.77 | 2.28 | Normal | Normal | Normal |
| E50G | 50 | 149 A > G | LAL167 | Unknown | Yes | No | 5.20 | 3.03 | 0.48 | 0.22 | Suspicious | Suspicious | Suspicious |
| L52V | 52 | 154 C > G | LAL168 | Unknown | Yes | Yes | 47.21 | 19.67 | 51.03 | 2.79 | Normal | Normal | Normal |

TABLE 4-continued

| Variant (Protein) | Residue | Variant (nucleic acid) | Plasmid ID | Pathogenic* | Western Blot Intracellular | Western Blot Secreted | Lipase Activity (% WT) Intracellular Mean | SD | Lipase Activity (% WT) Supernatant Mean | SD | Prediction** <8.5% intracellular activity | Prediction** <1.5% activity in supernatant | Prediction** Overall (<8.5% or <1.5% or both) |
|---|---|---|---|---|---|---|---|---|---|---|---|---|---|
| V53L | 53 | 157 G > C | LAL110 | Unknown | Yes | Low | 52.84 | 20.72 | 5.61 | 2.31 | Normal | Normal | Normal |
| V53A | 53 | 158 T > C | LAL169 | Unknown | Yes | Yes | 40.86 | 11.43 | 8.44 | 3.90 | Normal | Normal | Normal |
| V53G | 53 | 158 T > G | LAL109 | Unknown | Yes | No | 1.84 | 0.52 | 0.06 | 0.08 | Suspicious | Suspicious | Suspicious |
| D57G | 57 | 170 A > G | LAL111 | Unknown | Yes | No | −0.03 | 0.32 | 0.33 | 0.05 | Suspicious | Suspicious | Suspicious |
| D57V | 57 | 170 A > T | LAL083 | Yes | Yes | No | −0.05 | 0.19 | −0.06 | 0.30 | N/A | N/A | N/A |
| I60T | 60 | 179 T > C | LAL112 | Unknown | Yes | Low | 46.27 | 21.22 | 4.12 | 0.60 | Normal | Normal | Normal |
| R65X | 65 | 193 C > T | LAL064 | Yes | Low | No | 1.15 | 0.13 | 0.68 | 0.19 | N/A | N/A | N/A |
| G77D | 77 | 230 G > A | LAL171 | Unknown | Yes | Yes | 53.74 | 22.93 | 38.38 | 15.97 | Normal | Normal | Normal |
| V81L | 81 | 241 G > C | LAL172 | Unknown | Yes | Yes | 40.39 | 15.68 | 12.50 | 7.13 | Normal | Normal | Normal |
| V82I | 82 | 244 G > A | LAL173 | Unknown | Yes | Low | 32.46 | 15.56 | 1.61 | 1.07 | Normal | Normal | Normal |
| Q85K | 85 | 253 C > A | LAL101 | Yes | Yes | No | 0.60 | 0.80 | −0.03 | 0.14 | N/A | N/A | N/A |
| Q85R | 85 | 254 A > G | LAL065 | Yes | Yes | No | 0.63 | 0.19 | 0.47 | 0.35 | N/A | N/A | N/A |
| H86Y | 86 | 256 C > T | LAL093 | Yes | Yes | No | 0.29 | 0.80 | −0.15 | 0.23 | N/A | N/A | N/A |
| G87V | 87 | 260 G > T | LAL066 | Yes | Yes | No | 0.39 | 0.17 | 0.48 | 0.19 | N/A | N/A | N/A |
| L88F | 88 | 264 G > T | LAL174 | Unknown | Yes | Yes | 76.90 | 25.01 | 51.18 | 17.39 | Normal | Normal | Normal |
| S92C | 92 | 275 C > G | LAL175 | Unknown | Yes | Low | 26.21 | 10.18 | 1.14 | 0.37 | Normal | Suspicious | Suspicious |
| W95R | 95 | 283 T > A | LAL067 | Yes | Yes | No | 0.62 | 0.24 | 0.33 | 0.23 | N/A | N/A | N/A |
| N98K | 98 | 294 C > G | LAL102 | Yes | Yes | Low | 4.28 | 2.66 | −0.07 | 0.37 | N/A | N/A | N/A |
| N101S | 101 | 302 A > G | LAL177 | Unknown | Yes | Yes | 28.42 | 12.39 | 5.43 | 2.71 | Normal | Normal | Normal |
| S103R | 103 | 309 C > A | LAL094 | Yes | Yes | No | −0.07 | 0.03 | −0.03 | 0.17 | N/A | N/A | N/A |
| L104P | 104 | 311 T > C | LAL113 | Unknown | Yes | No | 42.89 | 14.09 | 2.58 | 0.99 | Normal | Normal | Normal |
| F106I | 106 | 316 T > A | LAL114 | Unknown | Yes | No | 7.15 | 2.08 | 0.03 | 0.20 | Suspicious | Suspicious | Suspicious |
| I107Hfs*4 | 107 | 317 ins T | LAL149 | Yes | Low | No | 0.52 | 0.67 | 0.10 | 0.15 | N/A | N/A | N/A |
| G112D | 112 | 335 G > A | LAL115 | Unknown | Yes | Yes | 73.22 | 12.45 | 16.90 | 6.55 | Normal | Normal | Normal |
| W116X | 116 | 347 G > A | LAL089 | Yes | Low | No | 0.44 | 0.40 | 0.13 | 0.03 | N/A | N/A | N/A |
| N119S | 119 | 356 A > G | LAL068 | Yes | Yes | No | 0.86 | 0.08 | 0.38 | 0.29 | N/A | N/A | N/A |
| R121G | 121 | 361 A > G | LAL090 | Yes | Yes | No | −0.20 | 0.44 | 0.04 | 0.19 | N/A | N/A | N/A |
| N123D | 123 | 367 A > G | LAL178 | Unknown | Yes | No | 3.47 | 1.61 | −0.01 | 0.28 | Suspicious | Suspicious | Suspicious |
| W125L | 125 | 374 G > T | LAL116 | Unknown | Yes | Yes | 71.08 | 22.00 | 12.09 | 3.81 | Normal | Normal | Normal |
| S126F | 126 | 377 C > T | LAL104 | Yes | Yes | No | 1.55 | 0.46 | 0.00 | 0.32 | N/A | N/A | N/A |
| R127W | 127 | 379 C > T | LAL117 | Unknown | Yes | No | 29.40 | 8.66 | 0.80 | 0.31 | Normal | Suspicious | Suspicious |
| H129P | 129 | 386 A > C | LAL070 | Yes | Yes | No | 0.83 | 0.39 | 0.08 | 0.60 | N/A | N/A | N/A |
| H129R | 129 | 386 A > G | LAL069 | Yes | Yes | No | 0.45 | 0.21 | 0.13 | 0.13 | N/A | N/A | N/A |
| S133X | 133 | 398 del C | LAL143 | Yes | Yes | Low | 0.03 | 0.67 | −0.09 | 0.09 | N/A | N/A | N/A |
| V134Ffs*4 | 134 | 397 del TC | LAL136 | Unknown | Yes | Low | 0.13 | 0.23 | −0.02 | 0.17 | Suspicious | Suspicious | Suspicious |
| Q136R | 136 | 407 A > G | LAL180 | Unknown | Yes | Yes | 32.95 | 9.88 | 13.97 | 4.26 | Normal | Normal | Normal |
| F139Ifs*7 | 139 | 414 ins A | LAL148 | Yes | Yes | Low | 0.63 | 0.54 | 0.06 | 0.24 | N/A | N/A | N/A |
| F139L | 139 | 417 C > A | LAL098 | Yes | Yes | No | 1.77 | 1.09 | 0.07 | 0.20 | N/A | N/A | N/A |
| W140X | 140 | 419 G > A | LAL071 | Yes | Yes | Low | 0.40 | 0.19 | 0.07 | 0.26 | N/A | N/A | N/A |
| D145N | 145 | 433 G > A | LAL118 | Unknown | Yes | Low | 25.87 | 4.35 | 1.80 | 0.37 | Normal | Normal | Normal |
| D145E | 145 | 435 T > A | LAL072 | Yes | Yes | Low | 4.96 | 3.13 | 1.17 | 0.47 | N/A | N/A | N/A |
| Y150C | 150 | 449 A > G | LAL119 | Unknown | Yes | Low | 33.85 | 12.34 | 0.62 | 0.44 | Normal | Suspicious | Suspicious |
| L152P | 152 | 455 T > C | LAL095 | Yes | Yes | No | 0.10 | 0.67 | 0.21 | 0.47 | N/A | N/A | N/A |
| F158C | 158 | 473 T > G | LAL120 | Unknown | Yes | No | 38.16 | 17.21 | 2.03 | 0.66 | Normal | Normal | Normal |
| N161Ifs*19 | 161 | 482 del A | LAL144 | Yes | Yes | No | 0.55 | 0.76 | −0.08 | 0.28 | N/A | N/A | N/A |
| V171L | 171 | 511 G > T | LAL181 | Unknown | Yes | Yes | 59.73 | 8.61 | 8.44 | 3.75 | Normal | Normal | Normal |
| G176S | 176 | 526 G > A | LAL096 | Yes | Yes | No | −0.13 | 0.11 | 0.32 | 0.27 | N/A | N/A | N/A |
| I182T | 182 | 545 T > C | LAL182 | Unknown | Yes | No | 15.25 | 2.15 | 0.40 | 0.09 | Normal | Suspicious | Suspicious |
| Q186R | 186 | 557 A > G | LAL183 | Unknown | Yes | Yes | 51.41 | 9.63 | 20.03 | 11.53 | Normal | Normal | Normal |
| A199Cfs*13 | 199 | 594 ins T | LAL147 | Yes | Yes | Low | 0.38 | 0.43 | 0.04 | 0.21 | N/A | N/A | N/A |
| L200P | 200 | 599 T > C | LAL073 | Yes | Yes | No | 0.18 | 0.64 | 0.00 | 0.34 | N/A | N/A | N/A |
| P202L | 202 | 605 C > T | LAL074 | Yes | Yes | No | 0.49 | 0.70 | 0.01 | 0.25 | N/A | N/A | N/A |
| V203L | 203 | 607 G > C | LAL099 | Yes | Yes | Yes | 43.19 | 17.45 | 158.20 | 54.80 | N/A | N/A | N/A |
| A204S | 204 | 610 G > T | LAL184 | Unknown | Yes | Yes | 56.86 | 11.36 | 19.22 | 5.87 | Normal | Normal | Normal |
| V206I | 206 | 616 G > A | LAL185 | Unknown | Yes | Yes | 61.32 | 5.30 | 61.30 | 34.61 | Normal | Normal | Normal |
| A207T | 207 | 619 G > A | LAL186 | Unknown | Yes | Yes | 100.76 | 21.90 | 148.76 | 45.48 | Normal | Normal | Normal |
| A207S | 207 | 619 G > T | LAL187 | Unknown | Yes | Yes | 91.67 | 18.61 | 115.18 | 38.36 | Normal | Normal | Normal |
| F208L | 208 | 624 C > G | LAL188 | Unknown | Yes | Yes | 87.25 | 9.96 | 40.72 | 12.12 | Normal | Normal | Normal |
| P212Lfs*5 | 212 | 635 del C | LAL137 | Yes | Yes | Low | 0.09 | 0.30 | 0.14 | 0.23 | N/A | N/A | N/A |
| R218G | 218 | 652 C > G | LAL189 | Unknown | Yes | Yes | 127.04 | 10.37 | 129.30 | 1.53 | Normal | Normal | Normal |
| R218X | 218 | 652 C > T | LAL075 | Yes | Yes | Yes | −0.15 | 0.32 | 0.04 | 0.08 | N/A | N/A | N/A |
| L219I | 219 | 655 T > A | LAL190 | Unknown | Yes | Yes | 109.47 | 27.92 | 119.62 | 17.51 | Normal | Normal | Normal |
| P220S | 220 | 658 C > T | LAL191 | Yes | Yes | Yes | 76.02 | 25.38 | 20.46 | 9.97 | N/A | N/A | N/A |
| F228L | 228 | 682 T > C | LAL192 | Unknown | Yes | Yes | 101.13 | 43.46 | 205.40 | 83.16 | Normal | Normal | Normal |
| F228C | 228 | 683 T > G | LAL121 | Unknown | Yes | Low | 28.91 | 17.66 | 1.80 | 0.11 | Normal | Normal | Normal |
| F228Lfs*13 | 228 | 684 del T | LAL138 | Yes | Yes | Low | −0.06 | 0.42 | 0.19 | 0.26 | N/A | N/A | N/A |
| G229R | 229 | 685 G > A | LAL133 | Unknown | Yes | Low | 28.13 | 7.50 | 5.15 | 2.68 | Normal | Normal | Normal |
| P235L | 235 | 704 C > T | LAL193 | Unknown | Yes | Yes | 44.69 | 10.51 | 5.50 | 2.77 | Normal | Normal | Normal |
| F239S | 239 | 716 T > C | LAL194 | Unknown | Yes | Yes | 66.88 | 29.95 | 223.13 | 115.35 | Normal | Normal | Normal |
| W242Gfs*12 | 242 | 724 del T | LAL142 | Yes | Low | Low | 0.11 | 0.53 | 0.03 | 0.36 | N/A | N/A | N/A |
| W242R | 242 | 724 T > C | LAL195 | Unknown | Yes | Yes | 43.15 | 10.57 | 109.04 | 43.10 | Normal | Normal | Normal |

TABLE 4-continued

| Variant (Protein) | Residue | Variant (nucleic acid) | Plasmid ID | Pathogenic* | Western Blot Intracellular | Western Blot Secreted | Lipase Activity (% WT) Intracellular Mean | Lipase Activity (% WT) Intracellular SD | Lipase Activity (% WT) Supernatant Mean | Lipase Activity (% WT) Supernatant SD | Prediction** <8.5% intracellular activity | Prediction** <1.5% activity in supernatant | Prediction** Overall (<8.5% or <1.5% or both) |
|---|---|---|---|---|---|---|---|---|---|---|---|---|---|
| H246R | 246 | 737 A > G | LAL196 | Unknown | Yes | Yes | 65.49 | 19.16 | 53.28 | 19.24 | Normal | Normal | Normal |
| V247I | 247 | 739 G > A | LAL197 | Unknown | Yes | Yes | 80.73 | 18.17 | 49.17 | 15.13 | Normal | Normal | Normal |
| V247D | 247 | 740 T > A | LAL198 | Unknown | Yes | Yes | 63.68 | 0.72 | 13.57 | 2.73 | Normal | Normal | Normal |
| T249I | 249 | 746 C > T | LAL199 | Unknown | Yes | Yes | 41.72 | 13.11 | 6.05 | 2.75 | Normal | Normal | Normal |
| H250D | 250 | 748 C > G | LAL200 | Unknown | Yes | Yes | 73.26 | 4.69 | 44.56 | 5.54 | Normal | Normal | Normal |
| H250P | 250 | 749 A > C | LAL201 | Unknown | Yes | Yes | 53.48 | 0.86 | 24.34 | 3.96 | Normal | Normal | Normal |
| I252M | 252 | 756 A > G | LAL202 | Unknown | Yes | Yes | 78.18 | 26.16 | 82.68 | 15.05 | Normal | Normal | Normal |
| K254M | 254 | 761 A > T | LAL203 | Unknown | Yes | Low | 60.00 | 3.21 | 0.61 | 0.02 | Normal | Suspicious | Suspicious |
| C257G | 257 | 769 T > G | LAL122 | Unknown | Yes | Low | 24.65 | 9.17 | 2.69 | 0.68 | Normal | Normal | Normal |
| G258R | 258 | 772 G > A | LAL204 | Unknown | Low | Yes | 116.25 | 29.12 | 298.43 | 99.33 | Normal | Normal | Normal |
| L264P | 264 | 791 T > C | LAL100 | Yes | Yes | Low | 74.93 | 17.07 | 0.39 | 0.38 | N/A | N/A | N/A |
| G266X | 266 | 796 G > T | LAL076 | Yes | Yes | Yes | 0.00 | 0.54 | −0.03 | 0.15 | N/A | N/A | N/A |
| E269D | 269 | 807 G > C | LAL205 | Unknown | Yes | Yes | 82.89 | 19.12 | 52.98 | 20.38 | Normal | Normal | Normal |
| N271H | 271 | 811 A > C | LAL084 | Yes | Yes | Yes | 47.21 | 20.46 | 6.27 | 2.00 | N/A | N/A | N/A |
| V279I | 279 | 835 G > A | LAL206 | Unknown | Yes | Yes | 43.74 | 6.53 | 13.49 | 6.22 | Normal | Normal | Normal |
| P285S | 285 | 853 C > T | LAL105 | Unknown | Yes | Yes | 74.44 | 4.25 | 108.28 | 38.24 | Normal | Normal | Normal |
| T288I | 288 | 863 C > T | LAL077 | Yes | Yes | Yes | 6.41 | 1.53 | 1.43 | 0.53 | N/A | N/A | N/A |
| S289C | 289 | 866 C > G | LAL078 | Yes | Yes | Low | 0.21 | 0.24 | 0.00 | 0.30 | N/A | N/A | N/A |
| Q291E | 291 | 871 C > G | LAL123 | Unknown | Yes | Low | 5.74 | 3.23 | 0.24 | 0.23 | Suspicious | Suspicious | Suspicious |
| M293V | 293 | 877 A > G | LAL207 | Unknown | Yes | Yes | 64.58 | 7.61 | 36.78 | 12.07 | Normal | Normal | Normal |
| L294S | 294 | 881 T > C | LAL079 | Yes | Yes | Yes | 0.59 | 0.58 | −0.16 | 0.24 | N/A | N/A | N/A |
| H295Y | 295 | 883 C > T | LAL080 | Yes | Yes | Low | 0.65 | 0.38 | −0.17 | 0.24 | N/A | N/A | N/A |
| S297C | 297 | 889 A > T | LAL134 | Unknown | Yes | Yes | 62.15 | 18.95 | 8.53 | 3.70 | Normal | Normal | Normal |
| Q298X | 298 | 892 C > T | LAL085 | Yes | Yes | Yes | 0.05 | 0.67 | 0.20 | 0.13 | N/A | N/A | N/A |
| Q298H | 298 | 894 G > C | LAL091 | Yes | Yes | Low | 6.32 | 3.30 | 0.59 | 0.23 | N/A | N/A | N/A |
| V300Nfs*30 | 300 | 898 del GTTA | LAL145 | Unknown | Yes | Low | 0.38 | 0.64 | 0.05 | 0.19 | Suspicious | Suspicious | Suspicious |
| A307D | 307 | 920 C > A | LAL124 | Unknown | Yes | Low | 2.22 | 1.25 | 0.10 | 0.09 | Suspicious | Suspicious | Suspicious |
| F308V | 308 | 922 T > G | LAL208 | Unknown | Yes | Low | 2.58 | 1.67 | 1.66 | 3.06 | Suspicious | Normal | Suspicious |
| G311R | 311 | 931 G > A | LAL097 | Yes | Yes | Low | 8.43 | 3.86 | 0.76 | 0.30 | N/A | N/A | N/A |
| K315R | 315 | 944 A > G | LAL210 | Unknown | Yes | Yes | 69.34 | 14.94 | 25.39 | 9.03 | Normal | Normal | Normal |
| K315N | 315 | 945 G > T | LAL211 | Unknown | Yes | Yes | 71.96 | 15.33 | 41.79 | 16.11 | Normal | Normal | Normal |
| Y317F | 317 | 950 A > T | LAL212 | Unknown | Yes | Yes | 70.81 | 10.90 | 69.40 | 25.35 | Normal | Normal | Normal |
| H319Y | 319 | 955 C > T | LAL213 | Unknown | Yes | Yes | 51.12 | 0.86 | 12.30 | 6.16 | Normal | Normal | Normal |
| Q322H | 322 | 966 G > C | LAL125 | Unknown | Yes | Low | 53.20 | 11.04 | 4.12 | 1.18 | Normal | Normal | Normal |
| Q322H | 322 | 966 G > C | LAL214 | Unknown | Yes | Yes | 34.43 | 10.77 | 3.78 | 1.67 | Normal | Normal | Normal |
| S323Lfs*44 | 323 | 967 del AG | LAL139 | Yes | Yes | Yes | −0.06 | 0.49 | 0.20 | 0.34 | N/A | N/A | N/A |
| Y324X | 324 | 972 T > A | LAL087 | Yes | Yes | Yes | −0.12 | 0.36 | 0.27 | 0.03 | N/A | N/A | N/A |
| P325L | 325 | 974 C > T | LAL103 | Yes | Yes | Low | 7.52 | 2.86 | 0.28 | 0.12 | N/A | N/A | N/A |
| T327Nfs*4 | 327 | 980 del C | LAL140 | Yes | Yes | Yes | −0.08 | 0.50 | 0.29 | 0.35 | N/A | N/A | N/A |
| K331E | 331 | 991 A > G | LAL216 | Unknown | Yes | Yes | 60.02 | 6.52 | 16.78 | 9.82 | Normal | Normal | Normal |
| P336L | 336 | 1007 C > T | LAL126 | Unknown | Yes | Low | 16.72 | 9.85 | 0.53 | 0.20 | Normal | Suspicious | Suspicious |
| T337A | 337 | 1009 A > G | LAL135 | Unknown | Yes | Low | 34.46 | 15.75 | 1.57 | 0.88 | Normal | Normal | Normal |
| S341G | 341 | 1021 A > G | LAL127 | Unknown | Yes | Low | 45.59 | 16.26 | 1.87 | 0.72 | Normal | Normal | Normal |
| G342R | 342 | 1024 G > A | LAL081 | Yes | Yes | Low | 0.02 | 0.54 | −0.14 | 0.35 | N/A | N/A | N/A |
| G342W | 342 | 1024 G > T | LAL088 | Yes | Yes | Low | −0.17 | 0.38 | 0.09 | 0.32 | N/A | N/A | N/A |
| G342V | 342 | 1025 G > T | LAL128 | Unknown | Yes | Low | 1.42 | 0.46 | −0.10 | 0.26 | Suspicious | Suspicious | Suspicious |
| G343Vfs*15 | 343 | 1028 del G | LAL141 | Yes | Yes | Low | −0.04 | 0.47 | 0.03 | 0.11 | N/A | N/A | N/A |
| G343D | 343 | 1028 G > A | LAL152 | Unknown | Low | No | 38.01 | 12.59 | 4.90 | 3.53 | Normal | Normal | Normal |
| H344R | 344 | 1031 A > G | LAL153 | Unknown | Yes | Yes | 75.52 | 27.36 | 172.12 | 62.91 | Normal | Normal | Normal |
| H344Q | 344 | 1032 C > G | LAL154 | Unknown | Yes | Yes | 80.44 | 20.96 | 71.42 | 30.78 | Normal | Normal | Normal |
| D345N | 345 | 1033 G > A | LAL092 | Yes | Yes | Low | −0.16 | 0.39 | 0.02 | 0.15 | N/A | N/A | N/A |
| A348V | 348 | 1043 C > T | LAL155 | Unknown | Yes | Low | 20.78 | 10.31 | 0.07 | 0.07 | Normal | Suspicious | Suspicious |
| L357P | 357 | 1070 T > C | LAL082 | Yes | Yes | No | 0.73 | 1.00 | −0.19 | 0.16 | N/A | N/A | N/A |
| I360N | 360 | 1079 T > A | LAL129 | Unknown | Yes | Low | 1.58 | 1.00 | −0.19 | 0.17 | Suspicious | Suspicious | Suspicious |
| I360T | 360 | 1079 T > C | LAL158 | Unknown | Yes | No | 14.32 | 3.36 | 0.40 | 0.10 | Normal | Suspicious | Suspicious |
| I369V | 369 | 1105 A > G | LAL159 | Unknown | Yes | Low | 39.24 | 5.86 | 3.27 | 0.61 | Normal | Normal | Normal |
| I369T | 369 | 1106 T > C | LAL160 | Unknown | Yes | No | 1.81 | 0.73 | 0.35 | 0.22 | Suspicious | Suspicious | Suspicious |
| P370L | 370 | 1109 C > T | LAL161 | Unknown | Yes | Low | 32.40 | 12.79 | 2.38 | 1.05 | Normal | Normal | Normal |
| P370Rfs*25 | 370 | 1109_1110 delCGinsG | LAL150 | Unknown | Low | No | 0.25 | 0.52 | 0.19 | 0.22 | Suspicious | Suspicious | Suspicious |
| H374Y | 374 | 1120 C > T | LAL130 | Unknown | Yes | Yes | 0.11 | 0.38 | 0.25 | 0.31 | Suspicious | Suspicious | Suspicious |
| L375P | 375 | 1124 T > C | LAL131 | Unknown | Yes | Low | 45.60 | 7.36 | 5.38 | 2.40 | Normal | Normal | Normal |
| I378T | 378 | 1133 T > C | LAL162 | Unknown | Yes | No | 11.44 | 5.16 | 0.58 | 0.16 | Normal | Suspicious | Suspicious |
| R386S | 386 | 1158 G > T | LAL163 | Unknown | Yes | Low | 8.83 | 2.41 | 0.30 | 0.19 | Normal | Suspicious | Suspicious |
| Y388C | 388 | 1163 A > G | LAL132 | Unknown | Yes | No | 1.07 | 0.78 | 0.37 | 0.24 | Suspicious | Suspicious | Suspicious |
| N389T | 389 | 1166 A > C | LAL164 | Unknown | Yes | Yes | 47.45 | 14.42 | 31.16 | 6.95 | Normal | Normal | Normal |
| WT | | WT | LAL063 | No | Yes | Yes | 100.00 | 27.75 | 100.00 | 30.86 | N/A | N/A | N/A |

*Pathogenicity status reflects information known to the inventors but not necessarily publicly known or available
**Pathogenicity predictions are shown as "N/A" for mutations whose pathogenicity status has been characterized as pathogenic or non-pathogenic Experimental Expression of LIPA Variants. Plasmids encoding WT LIPA and LIPA variants with C-terminal 6x histidine tags were ordered from Thermo Fisher Scientific GeneArt (Regensburg, Germany). Plasmids were sequence verified to confirm the presence of desired mutations. Constructs were transiently transfected into Expi293F cells using Expi-Fectamine 293 and the methodology recommended by the manufacturer (Thermo Fisher Scientific, Carlsbad, Calif.). Transfections were carried out at the two milliliter scale in 12-well tissue culture plates (Fisher Scientific, Waltham, Mass.). Transfected cultures were harvested three days post-transfection. Briefly, cultures were spun down at 500xg for five minutes, supernatants transferred to fresh plates, and cell pellets washed twice in phosphate-buffered saline (PBS, GE Healthcare, Marlborough, Mass.). Transfected cultures were incubated with 0.5 mL lysis buffer [1% Triton X-100, 10 mM Sodium Phosphate (pH 7.0), 10 mM dithiothreitol (DTT) and 1 mM ethylenediaminetetraacetic acid (EDTA) in water] for 45 minutes at 4° C. and centrifuged for 15 minutes at 3,000xg to remove insoluble materials.

Western Blot. Cell lysates and supernatants from transfected cultures were mixed with 4x E-PAGE loading buffer and run on 48-well E-PAGE 8% Protein Gels (Thermo Fisher Scientific). Proteins were transferred to polyvinylidene fluoride (PVDF) membranes (Thermo Fisher Scientific), which were incubated overnight in blocking buffer [1% bovine serum albumin (BSA), 0.05% Tween-20 (both Sigma-Aldrich, St. Louis, Mo.) in PBS] at 4° C. Membranes were probed with 1 µg/mL of mouse monoclonal anti-6x his tag antibody (Abcam, Cambridge, Mass.) in wash buffer [0.3% BSA, 0.05% Tween-20 in PBS] for 60 minutes, washed five times, incubated with 0.1 µg/mL IRDye 680RD Donkey anti-mouse IgG (H+L) (LiCor, Lincoln, Nebr.) for thirty minutes and washed four times in wash buffer and once in PBS. His-tagged proteins were detected by near-infrared fluorescence of the secondary antibody using the Odyssey CLx (LiCor).

LAL Enzyme Assay. Cell lysates and supernatants from transfected cultures were diluted 25 fold in assay buffer [200 mM Sodium Acetate (pH 5.5), 1% Triton X-100, and 1% human serum albumin]. 10 µl of this dilution was added to 40 µl assay buffer in a black 384 well Optiplate (Perkin Elmer, Waltham, Mass.) for a total dilution of 150 fold. The LAL reaction was started by adding 10 µl of the substrate 4-methylumbelliferyl (4-MU) oleate (Sigma-Aldrich) to a final concentration of 100 µM in a total reaction volume of 60 µl. A BioTek Synergy 2 plate reader was used to follow 4-methylumbelliferyl fluorophore production at excitation/emission wavelengths of 360/460+/−40 nm. The initial velocity for each LAL variant was determined from the first 10 to 20 minutes of the reaction and then normalized to total cell lysate protein content as measured by BCA assay (Pierce). Finally, all data was expressed relative to the WT sample.

Summary of Results

Rank order of the LAL variants based on intracellular lipase activity is shown in FIG. 2, and based on secreted lipase activity in FIG. 3. Results from the 4-MU oleate activity assays and the Western blot assays for LIPA variants are reported in Table 4. Pathogenicity status (i.e., pathogenic, non-pathogenic, or unknown) reflects information known to the inventors but not necessarily publicly known or available.

Of the known pathogenic mutations, 49 (~91%) exhibited less than 8.5% intracellular lipase activity compared to wild type (5 outliers), and 50 (~93%) exhibited less than 1.5% lipase activity in supernatant compared to wild type (4 outliers).

Some variants (including some with confirmed pathogenic mutations) showed intracellular activity, but were not secreted. Therefore, both intracellular lipase activity and secreted lipase activity are taken into account when predicting pathogenicity.

Of the unknown variants, 30 are predicted to be pathogenic, based on criteria of less than <8.5% intracellular activity or <1.5% activity in supernatants.

There is a possibility that additional unknown variants are pathogenic, but may have been missed in this assay. For example, some known pathogenic variants shows relatively normal lipase activity (e.g. V203L and P220S)—thus in some instances there may be other factors beyond lipase activity that contribute to pathogenicity.

ADDITIONAL REFERENCES

Balwani et al., Hepatology. 2013 September; 58(3):950-7. Epub 2013 Mar. 28.
Burton et al., N Engl J Med. 2015 Sep. 10; 373(11):1010-20
Valayannopoulos et al., J Hepatol. 2014 November; 61(5): 1135-42.Epub 2014 Jun. 30.

Example III

Structural Mapping of Missense Variants

Example II (Table 4) shows LAL activity assay results for over 50 LIPA variants known to be pathogenic. Most of these pathogenic variants exhibited LAL activity levels in a cell lysate assay that were below 10% of the wild-type level; however, 5 of the known pathogenic variants surprisingly showed relatively normal LAL activity.

A three dimensional structure for human LAL was prepared using homology modeling techniques, with the solved three-dimensional structure for canine LAL (PDB:1K8Q) serving as the reference structure (FIG. 4, panel A) (Roussel et al., 1999, J. Biol. Chem. 274(24):16995-17002; see also Azam et al., Comb. Chem. High Throughput Screen., 2014, 17(5):473-482; and Roussel et al., J. Biol. Chem., 2002, 277(3):2266-2274). The three-dimensional human LAL protein structure shows a catalytic domain and a lid domain.

Known pathogenic LAL missense variants as described in Example II were mapped to the human LAL homology model. All missense mutations that exhibited LAL activity levels of below the cutoff value of 10% of wild-type LAL activity in the cell lysate assay were found to be localized to the catalytic domain of the LAL molecule (FIG. 4, panel B). However, of the five clinically confirmed pathogenic variants that displayed relatively normal levels of LAL activity, four were found to be localized to the lid domain (residues 206-271 in human LAL) instead of the catalytic domain (FIG. 4, panel C), and the fifth (at position 203), is in close proximity to the lid domain, suggesting that an alternative explanation for pathogenicity may exist. The lid domain may be responsible for substrate binding. We conclude that missense mutations in the lid domain may adversely impact the binding of the natural substrates for LAL (e.g., cholesterol esters and triglycerides), resulting in a reduction in lipase activity in vivo, even though these LIPA variants appear capable of binding and catalyzing cleavage of the artificial substrate (4-MU oleate) in the in vitro cell lysate assay.

To reevaluate whether mutations in previously uncharacterized LIPA gene variants which were classified as "normal" in Example II may instead be potentially pathogenic, a LAL activity assay that employs a natural substrate, such as a cholesteryl oleate or a triacylglycerol, rather than an artificial substrate, such as 4-MU oleate, can be used to assess LAL activity. Exemplary assays for LAL activity utilizing cholesteryl oleate or triacylglcerol (such as trioleoylglycerol, also known as triolein) as substrates are set forth in Doolittle et al., "Lipase and Phospholipase Protocols" in Meth. Mol. Biol., Human Press, 1999, 109:98-102; and Sando et al., J. Biol. Chem., 1985, 15186-93. An exemplary cholesteryl oleate assay is described in Example IV.

Example IV

Cholesteryl Oleate Assay

Reagents used in an exemplary cholesteryl oleate assay are Amplex Red Cholesterol Assay Kit (Life Technologies Catalog #A12216), Nonaethylene Glycol Monododecyl Ether (NGME) (Sigma Cat: P9641-50g), and Albumin (human serum), USP, 25% Solution (Baxter Cat: 1500233).

Solutions used in the assay are as follows:
0.1M phosphate buffer pH7.0: Dissolve 5.36 g of sodium phosphate dibasic heptahydrate in about 160 ml milliQ water, adjust pH to 7.0 with HCl, adjust the final volume to 200 ml with milliQ water
Enzyme Reaction Stop Solution: 0.77 M Tris-HCl pH8.0 (optional)
Enzyme Reaction Buffer (ERB): 0.2M Sodium Acetate, pH5.5, 1% HSA
1×Amplex Red Buffer (ARB): Dilute 10 ml 5× Buffer (supplied with the Amplex Red Cholesterol Assay Kit) with 40 ml of milliQ water.

Prior to first use, reagents in the Amplex Red Cholesterol Assay kit are aliquoted as follows:
20 mM Amplex Red reagent: Dissolve one vial containing 1 mg lyophilized Amplex Red reagent with 200 µl DMSO provided in the kit. Aliquot 85 µl/tube, and store in −20° C. freezer
HRP (200 U/ml): Dissolve 200 U of lyophilized HRP in 1 ml of 1×Amplex Red Buffer. Aliquot 200 µl/tube, and store in −20° C. freezer.
Cholesterol Oxidase (200 U/ml): Dissolve 50 U of Lyophilized cholesterol oxidase in 250 µl of 1×Amplex Red Buffer, Aliquot to 55 µl/tube, and store in −20° C. freezer
Cholesterol Calibration Stock Solution: Aliquot 8 µl/tube Cholesterol Reference Standard provided with the Amplex Red kit.

Stock and dilution solutions are prepared as follows:
Cholesteryl Oleate (CO) Stock Solution (10 mM). NGME is melted at 37° C. until completely liquid. Phosphate buffer (0.1M, 9 ml) is warmed to 75° C. for 10 minutes. NGME (3 ml) is warmed to 75° C. for 10 minutes. Cholesteryl Oleate (65.0 mg) is placed into a 15 ml Corning tube. Molten NGME (1 ml) is added to the 15 ml tube containing Cholesteryl Oleate and the solution is incubated for 10 minutes. After the Cholesteryl Oleate has completely dissolved in NGME, the solution is diluted with 9 ml of 75° C. 0.1M Phosphate Buffer and maintained at 75° C. with occasional mixing for 10 minutes. The solution is removed from the water bath and the tube is inverted until the solution becomes clear. The solution is stored at room temperature until use, and is discarded after 16 hours.

Cholesteryl Oleate (CO) Dilution Solution. NGME (1 ml, warmed to 75° C.) and 9 ml 0.1M phosphate buffer (warmed to 75° C.) are combined and mixed well to make a dilution solution.

Enzymatic activity is assayed in using 96 well plates according to the following procedure. Immediately preceding the assay, samples or standards are diluted to 11 µg/mL with ERB (0.2M Sodium Acetate, pH5.5, 1% HSA). The CO stock solution (10 mM) is diluted to concentrations of 0.625 mM, 1.25 mM, 2.5 mM and 5 mM with dilution solution. In the sample wells, 90 µL of enzyme sample (11 µg/mL) is combined with 10 µL the CO dilutions; in the wells containing a wild-type LAL standard, such as sebelipase alfa, 90 µL of enzyme standard (11 µg/mL) is combined with 10 µL the CO dilutions; in substrate background wells, 90 µL of ERB (0.2M Sodium Acetate, pH 5.5, 1% HSA) is combined with 10 µL of the CO dilutions. The mixtures are incubated at 37° C. for 30 minutes.

During the incubation period, a detection plate with black walls is prepared as follows. A product detection cocktail (300 µM Amplex Red reagent, 2 U/ml HRP, 2 U/ml Cholesterol Oxidase) is prepared by combining 5.31 ml of 1×Amplex Red Buffer, 82.5 µl of 20 mM Amplex Red Reagent, 55 µl of the 200 U/ml HRP Reagent, and 55 µl of the 200 U/ml Cholesterol Oxidase Reagent and kept at room temperature for no more than 60 minutes prior to use.

Cholesterol serial dilutions for a calibration curve are prepared as follows:

| Cholesterol concentration (µM) | µL of 40 µM cholesterol stock | µL previous dilution | µL ARB | Final Concentration in detection plate (µM) |
|---|---|---|---|---|
| 40 | 200 | — | — | 16 |
| 20 | 200 | — | 200 | 8 |
| 10 | — | 200 | 200 | 4 |
| 5 | — | 200 | 200 | 2 |
| 2.5 | — | 200 | 200 | 1 |
| 1.25 | — | 200 | 200 | 0.5 |
| 0.625 | — | 200 | 200 | 0.25 |
| 0 (Blank) | — | — | 200 | 0 |

At the end of the incubation time, 50 µl of Enzyme Reaction Stop Solution (0.77M Tris-HCl pH8.0) is optionally added to each well of reaction plate.

In wells of the detection plate that correspond with wells of the reaction plate, ARB (40 µl) is added, then 10 µL from each well of the reaction plate.

In the cholesterol standards wells, 10 µl of Mock Enzyme solution (Enzyme Reaction buffer:CO dilution solution=9:1) is combined with 40 µl in duplicate or triplicate of the cholesterol Calibration standard solutions.

Product Detection Cocktail (Amplex Red/HRP/Cholesterol Oxidase in ARB, 50 µL) is then added to all wells in detection plate, and the detection plate is incubated at 37° C. for 5 minutes. An endpoint reading is established at Ex 540 nm, Em 590 nm.

The complete disclosures of all patents, patent applications including provisional patent applications, publications including patent publications and nonpatent publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference.

The foregoing detailed description and examples have been given for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A method for treating a patient afflicted with or suspected of being afflicted with LAL-D, the method comprising:
administering a therapeutically effective amount of a recombinant human LAL to the patient, wherein the patient has at least one LIPA allelic variant, wherein the at least one LIPA allelic variant comprises a nucleotide sequence mutation encoding an amino acid substitution at amino acid position A307 relative to the wild-type LAL amino acid sequence (SEQ ID NO:2).

2. The method of claim 1, wherein the mutation comprises a lysosomal acid lipase (LAL) activity-reducing mutation.

3. The method of claim 1, wherein the mutation occurs in combination with a second mutation in the human LIPA nucleotide sequence.

4. The method of claim 3, wherein the second mutation comprises c.894G>A common exon 8 splice junction mutation (E8SJM).

5. The method of claim 1, wherein the mutation does not cause a frame shift.

6. The method of claim 1, wherein the mutation causes a frame shift.

7. The method of claim 1, wherein the recombinant human LAL comprises sebelipase alfa.

8. The method of claim 1, wherein the patient is a pediatric patient.

9. The method of claim 1, wherein the patient is an adult patient.

10. The method of claim 1, wherein the patient is afflicted with Wolman Disease or Cholesteryl Ester Storage Disease (CESD).

11. The method of claim 1, wherein the amino acid substitution at amino acid position A307 comprises an A307D amino acid substitution.

12. The method of claim 1, the method further comprising:
    (a) providing a biological sample obtained from the patient, the biological sample comprising a nucleic acid; and
    (b) performing a genetic analysis on the biological sample to detect the presence of a mutation in a human LIPA nucleotide sequence, wherein the mutation comprises a nucleotide sequence mutation encoding an amino acid substitution at amino acid position A307 relative to the wild-type LAL amino acid sequence (SEQ ID NO:2).

13. The method of claim 12, wherein performing a genetic analysis on the biological sample comprises performing whole transcriptome sequencing, whole exome sequencing, whole genome sequencing, or hybridization to a DNA microarray.

14. The method of claim 11, the method further comprising:
    (a) providing a biological sample obtained from the patient, the biological sample comprising a nucleic acid; and
    (b) performing a genetic analysis on the biological sample to detect the presence of a mutation in a human LIPA nucleotide sequence, wherein the mutation comprises a nucleotide sequence mutation encoding an A307D amino acid substitution at amino acid position A307 relative to the wild-type LAL amino acid sequence (SEQ ID NO:2).

15. The method of claim 14, wherein performing a genetic analysis on the biological sample comprises performing whole transcriptome sequencing, whole exome sequencing, whole genome sequencing, or hybridization to a DNA microarray.

16. The method of claim 11, wherein the recombinant human LAL comprises sebelipase alfa.

17. The method of claim 11, wherein the patient is a pediatric patient.

18. The method of claim 11, wherein the patient is an adult patient.

19. The method of claim 11, wherein the patient is afflicted with Wolman Disease or Cholesteryl Ester Storage Disease (CESD).

20. The method of claim 11, wherein the mutation occurs in combination with a second mutation in the human LIPA nucleotide sequence.

21. The method of claim 20, wherein the second mutation comprises c.894G>A common exon 8 splice junction mutation (E8SJM).

* * * * *